US012735462B2

(12) United States Patent
So et al.

(10) Patent No.: US 12,735,462 B2
(45) Date of Patent: Sep. 15, 2026

(54) GlxR PROTEIN VARIANT OR THREONINE PRODUCTION METHOD USING SAME

(71) Applicant: CJ CheilJedang Corporation, Seoul (KR)

(72) Inventors: Yee-Seul So, Seoul (KR); Su Yon Kwon, Seoul (KR); Kwang Woo Lee, Seoul (KR); Jihyun Shim, Seoul (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 441 days.

(21) Appl. No.: 18/271,292

(22) PCT Filed: Jan. 6, 2022

(86) PCT No.: PCT/KR2022/000204

§ 371 (c)(1),
(2) Date: Jul. 7, 2023

(87) PCT Pub. No.: WO2022/149865

PCT Pub. Date: Jul. 14, 2022

(65) Prior Publication Data

US 2025/0326803 A1 Oct. 23, 2025

(30) Foreign Application Priority Data

Jan. 11, 2021 (KR) ........................ 10-2021-0003609

(51) Int. Cl.
*C07K 14/34* (2006.01)
*C12N 1/20* (2026.01)
*C12N 15/77* (2006.01)
*C12P 13/08* (2006.01)

(52) U.S. Cl.
CPC ................ *C07K 14/34* (2013.01); *C12N 1/20* (2013.01); *C12N 15/77* (2013.01); *C12P 13/08* (2013.01)

(58) Field of Classification Search
None
See application file for complete search history.

(56) References Cited

U.S. PATENT DOCUMENTS 7,566,557 B2 7/2009 Klopprogge et al.
2005/0196847 A1* 9/2005 Klopprogge ........... C07K 14/34 435/115
2008/0280333 A1 11/2008 Klopprogge et al.
2016/0369310 A1 12/2016 Lee et al.

FOREIGN PATENT DOCUMENTS

CN 1656117 A 8/2005
CN 111491945 A 8/2020
EP 3686215 A1 7/2020
JP 2005-536194 A 12/2005
JP 2008-522611 A 7/2008
JP 2018-113966 A 7/2018
KR 10-2005-0026388 A 3/2005
KR 10-2008-0025355 3/2008
KR 10-2008-0082880 9/2008
KR 10-2011-0058731 6/2011
KR 10-2020-0130567 A 11/2020
WO 2020/138815 A1 7/2020

OTHER PUBLICATIONS

Park SY, Moon MW, Subhadra B, Lee JK. Functional characterization of the glxR deletion mutant of Corynebacterium glutamicum ATCC 13032: involvement of GlxR in acetate metabolism and carbon catabolite repression. FEMS Microbiol Lett. Mar. 2010;304(2): 107-15. (Year: 2010).*
Kohl et al (Journal of Biotechnology 135 (2008) 340-350) (Year: 2008).*
Office Action issued Nov. 1, 2023 for Australian Patent Application No. 2022206623.
Rice et al., "EMBOSS: The European Molecular Biology Open Software Suite," Trends Genet., 16: 276-277 (2000).
Needleman et al., "A General Method Applicable to the Search for Similarities in the Amino Acid Sequence of Two Proteins," J. Mol. Biol., 48: 443-453 (1970).
Devereux et al., "A comprehensive set of sequence analysis programs for the VAX," Nucleic Acids Research, 12: 387 (1984).
Smith et al., "Comparison of Biosequences, " Adv. Appl. Math, 2: 482 (1981).
Gribskov et al., "Sigma factors from *E. coli, B. subtils*, phage SP01, and phage T4 are homologous proteins," Nucl. Acids Res., 14: 6745 (1986).
Sambrook et al., "Molecular Cloning, A Laboratory Manual," 2nd Edition, Cold Spring Harbor Laboratory press, Cold Spring Harbor, New York (1989).
Ausubel et al., "Current Protocols in Molecular Biology," John Wiley & Sons, Inc., New York (1989).
Sambrook et al., supra,9.50-9.51, 11.7-11.8 (1989).
International Search Report issued in corresponding International Patent Application No. PCT/KR2022/000204 dated Jul. 7, 2022.
Kim et al., "Identification and Characterization of glxR, a Gene Involved in Regulation of Glyoxylate Bypass in Corynebacterium glutamicum", Journal of Bacteriology, vol. 186, No. 11, Jun. 2004, pp. 3453-3460.
Park et al., "Functional characterization of the g/xR deletion mutant of Corynebacterium glutamicum ATCC 13032: involvement of GlxR in acetate metabolism and carbon catabolite repression", FEMS Microbiol Lett, vol. 304, 2010, pp. 107-115.
Rhodius et al., "Transcription Activation by the *Escherichia coli* Cyclic AMP Receptor Protein: Determinants within Activating Region 3", J. Mol. Biol., vol. 299, 2000, pp. 295-310.

(Continued)

*Primary Examiner* — Thomas J. Visone
*Assistant Examiner* — Georgiana C Reglas
(74) *Attorney, Agent, or Firm* — Morgan, Lewis & Bockius LLP

(57) ABSTRACT

The present application relates to a GlxR protein variant or a threonine production method using same, and the GlxR protein variant according to one embodiment is introduced into a microorganism to reduce by-product output and remarkably increase threonine production capacity.

20 Claims, No Drawings

Specification includes a Sequence Listing.

(56) References Cited

OTHER PUBLICATIONS

Zhou et al., "Identification of the activating region of catabolite gene activator protein (CAP): Isolation and characterization of mutants of CAP specifically defective in transcription activation", Proc. Natl. Acad. Sci. USA, Biochemistry, vol. 90, Jul. 1993, pp. 6081-6085.
Office Action issued in corresponding Japanese Patent Application No. 2023-541941, dated Jul. 30, 2024.
Notice of Allowance issued in corresponding Japanese Patent Application No. 2023-541941, dated Oct. 8, 2024.
GSP Database, "*Escherichia* sp. Crp E35A mutant protein, Seq ID 3.", Database Accession No. BGJ29861, Jun. 19, 2019, 1 page.
Dong et al., "Metabolic engineering of *Escherichia coli* and *Corynebacterium glutamicum* for the production of L-threonine", Biotechnology Advances, vol. 29, 2011, pp. 11-23.
Extended European Search Report issued in corresponding European Patent Application No. 22736842.0, dated Jun. 5, 2025.

* cited by examiner

SEQUENCE LISTING

```
<160> NUMBER OF SEQ ID NOS: 55

<210> SEQ ID NO 1
<211> LENGTH: 227
<212> TYPE: PRT
<213> ORGANISM: Artificial Sequence
<220> FEATURE:
<223> OTHER INFORMATION: GlxR_amino acid

<400> SEQUENCE: 1

Met Glu Gly Val Gln Glu Ile Leu Ser Arg Ala Gly Ile Phe Gln Gly
1               5                   10                  15

Val Asp Pro Thr Ala Val Asn Asn Leu Ile Gln Asp Met Glu Thr Val
            20                  25                  30

Arg Phe Pro Arg Gly Ala Thr Ile Phe Asp Glu Gly Glu Pro Gly Asp
        35                  40                  45

Arg Leu Tyr Ile Ile Thr Ser Gly Lys Val Lys Leu Ala Arg His Ala
    50                  55                  60

Pro Asp Gly Arg Glu Asn Leu Leu Thr Ile Met Gly Pro Ser Asp Met
65                  70                  75                  80

Phe Gly Glu Leu Ser Ile Phe Asp Pro Gly Pro Arg Thr Ser Ser Ala
                85                  90                  95

Val Cys Val Thr Glu Val His Ala Ala Thr Met Asn Ser Asp Met Leu
            100                 105                 110

Arg Asn Trp Val Ala Asp His Pro Ala Ile Ala Glu Gln Leu Leu Arg
        115                 120                 125

Val Leu Ala Arg Arg Leu Arg Arg Thr Asn Ala Ser Leu Ala Asp Leu
    130                 135                 140

Ile Phe Thr Asp Val Pro Gly Arg Val Ala Lys Thr Leu Leu Gln Leu
145                 150                 155                 160

Ala Asn Arg Phe Gly Thr Gln Glu Ala Gly Ala Leu Arg Val Asn His
                165                 170                 175
```

```
Asp Leu Thr Gln Glu Glu Ile Ala Gln Leu Val Gly Ala Ser Arg Glu
            180                 185                 190

Thr Val Asn Lys Ala Leu Ala Thr Phe Ala His Arg Gly Trp Ile Arg
        195                 200                 205

Leu Glu Gly Lys Ser Val Leu Ile Val Asp Thr Glu His Leu Ala Arg
    210                 215                 220

Arg Ala Arg
225


<210> SEQ ID NO 2
<211> LENGTH: 684
<212> TYPE: DNA
<213> ORGANISM: Artificial Sequence
<220> FEATURE:
<223> OTHER INFORMATION: glxR_nucleic acid

<400> SEQUENCE: 2

gtggaaggtg tacaggagat cctgtcgcgc gccggaattt ttcaaggcgt tgacccaacg      60

gcagtcaata acctcatcca ggatatggag accgttcgct tcccacgcgg agcaaccatc     120

ttcgacgagg gcgagccagg tgaccgcctt tacatcatca cctccggcaa agtgaagctt     180

gcgcgccacg caccggacgg ccgcgaaaac ctgctgacca tcatgggtcc ttccgacatg     240

ttcggtgagc tctccatctt cgacccaggc ccacgcacct cctctgcagt gtgtgtcacc     300

gaagttcatg cagcaaccat gaactctgac atgctgcgca actgggtagc tgaccaccca     360

gctatcgctg agcagctcct gcgcgttctg gctcgtcgtc tgcgtcgcac caacgcttcc     420

ctggctgacc tcatcttcac cgacgtccca ggccgcgttg ctaagaccct tctgcagctg     480

gctaaccgct tcggcaccca agaagctggc gcgctgcgcg tgaaccacga cctcactcag     540

gaagaaatcg cacagctcgt cggtgcttcc cgtgaaactg tgaataaggc tcttgcaacg     600

ttcgcacacc gtggctggat tcgcctcgag ggcaagtccg tcctcattgt ggacaccgag     660

catttggcac gtcgcgctcg ataa                                            684


<210> SEQ ID NO 3
<211> LENGTH: 227
<212> TYPE: PRT
<213> ORGANISM: Artificial Sequence
<220> FEATURE:
<223> OTHER INFORMATION: GlxR_E45A

<400> SEQUENCE: 3

Met Glu Gly Val Gln Glu Ile Leu Ser Arg Ala Gly Ile Phe Gln Gly
1               5                   10                  15

Val Asp Pro Thr Ala Val Asn Asn Leu Ile Gln Asp Met Glu Thr Val
            20                  25                  30

Arg Phe Pro Arg Gly Ala Thr Ile Phe Asp Glu Gly Ala Pro Gly Asp
        35                  40                  45

Arg Leu Tyr Ile Ile Thr Ser Gly Lys Val Lys Leu Ala Arg His Ala
    50                  55                  60

Pro Asp Gly Arg Glu Asn Leu Leu Thr Ile Met Gly Pro Ser Asp Met
65                  70                  75                  80

Phe Gly Glu Leu Ser Ile Phe Asp Pro Gly Pro Arg Thr Ser Ser Ala
                85                  90                  95

Val Cys Val Thr Glu Val His Ala Ala Thr Met Asn Ser Asp Met Leu
            100                 105                 110

Arg Asn Trp Val Ala Asp His Pro Ala Ile Ala Glu Gln Leu Leu Arg
        115                 120                 125
```

```
Val Leu Ala Arg Arg Leu Arg Arg Thr Asn Ala Ser Leu Ala Asp Leu
    130                 135                 140

Ile Phe Thr Asp Val Pro Gly Arg Val Ala Lys Thr Leu Leu Gln Leu
145                 150                 155                 160

Ala Asn Arg Phe Gly Thr Gln Glu Ala Gly Ala Leu Arg Val Asn His
                165                 170                 175

Asp Leu Thr Gln Glu Glu Ile Ala Gln Leu Val Gly Ala Ser Arg Glu
            180                 185                 190

Thr Val Asn Lys Ala Leu Ala Thr Phe Ala His Arg Gly Trp Ile Arg
        195                 200                 205

Leu Glu Gly Lys Ser Val Leu Ile Val Asp Thr Glu His Leu Ala Arg
    210                 215                 220

Arg Ala Arg
225


<210> SEQ ID NO 4
<211> LENGTH: 227
<212> TYPE: PRT
<213> ORGANISM: Artificial Sequence
<220> FEATURE:
<223> OTHER INFORMATION: GlxR_E45S

<400> SEQUENCE: 4

Met Glu Gly Val Gln Glu Ile Leu Ser Arg Ala Gly Ile Phe Gln Gly
1               5                   10                  15

Val Asp Pro Thr Ala Val Asn Asn Leu Ile Gln Asp Met Glu Thr Val
            20                  25                  30

Arg Phe Pro Arg Gly Ala Thr Ile Phe Asp Glu Gly Ser Pro Gly Asp
        35                  40                  45

Arg Leu Tyr Ile Ile Thr Ser Gly Lys Val Lys Leu Ala Arg His Ala
    50                  55                  60

Pro Asp Gly Arg Glu Asn Leu Leu Thr Ile Met Gly Pro Ser Asp Met
65                  70                  75                  80

Phe Gly Glu Leu Ser Ile Phe Asp Pro Gly Pro Arg Thr Ser Ser Ala
                85                  90                  95

Val Cys Val Thr Glu Val His Ala Ala Thr Met Asn Ser Asp Met Leu
            100                 105                 110

Arg Asn Trp Val Ala Asp His Pro Ala Ile Ala Glu Gln Leu Leu Arg
        115                 120                 125

Val Leu Ala Arg Arg Leu Arg Arg Thr Asn Ala Ser Leu Ala Asp Leu
    130                 135                 140

Ile Phe Thr Asp Val Pro Gly Arg Val Ala Lys Thr Leu Leu Gln Leu
145                 150                 155                 160

Ala Asn Arg Phe Gly Thr Gln Glu Ala Gly Ala Leu Arg Val Asn His
                165                 170                 175

Asp Leu Thr Gln Glu Glu Ile Ala Gln Leu Val Gly Ala Ser Arg Glu
            180                 185                 190

Thr Val Asn Lys Ala Leu Ala Thr Phe Ala His Arg Gly Trp Ile Arg
        195                 200                 205

Leu Glu Gly Lys Ser Val Leu Ile Val Asp Thr Glu His Leu Ala Arg
    210                 215                 220

Arg Ala Arg
225


<210> SEQ ID NO 5
```

<211> LENGTH: 227
<212> TYPE: PRT
<213> ORGANISM: Artificial Sequence
<220> FEATURE:
<223> OTHER INFORMATION: GlxR_E45F

<400> SEQUENCE: 5

```
Met Glu Gly Val Gln Glu Ile Leu Ser Arg Ala Gly Ile Phe Gln Gly
1               5                   10                  15

Val Asp Pro Thr Ala Val Asn Asn Leu Ile Gln Asp Met Glu Thr Val
            20                  25                  30

Arg Phe Pro Arg Gly Ala Thr Ile Phe Asp Glu Gly Phe Pro Gly Asp
        35                  40                  45

Arg Leu Tyr Ile Ile Thr Ser Gly Lys Val Lys Leu Ala Arg His Ala
    50                  55                  60

Pro Asp Gly Arg Glu Asn Leu Leu Thr Ile Met Gly Pro Ser Asp Met
65                  70                  75                  80

Phe Gly Glu Leu Ser Ile Phe Asp Pro Gly Pro Arg Thr Ser Ser Ala
                85                  90                  95

Val Cys Val Thr Glu Val His Ala Ala Thr Met Asn Ser Asp Met Leu
            100                 105                 110

Arg Asn Trp Val Ala Asp His Pro Ala Ile Ala Glu Gln Leu Leu Arg
        115                 120                 125

Val Leu Ala Arg Arg Leu Arg Arg Thr Asn Ala Ser Leu Ala Asp Leu
    130                 135                 140

Ile Phe Thr Asp Val Pro Gly Arg Val Ala Lys Thr Leu Leu Gln Leu
145                 150                 155                 160

Ala Asn Arg Phe Gly Thr Gln Glu Ala Gly Ala Leu Arg Val Asn His
                165                 170                 175

Asp Leu Thr Gln Glu Glu Ile Ala Gln Leu Val Gly Ala Ser Arg Glu
            180                 185                 190

Thr Val Asn Lys Ala Leu Ala Thr Phe Ala His Arg Gly Trp Ile Arg
        195                 200                 205

Leu Glu Gly Lys Ser Val Leu Ile Val Asp Thr Glu His Leu Ala Arg
    210                 215                 220

Arg Ala Arg
225
```

<210> SEQ ID NO 6
<211> LENGTH: 227
<212> TYPE: PRT
<213> ORGANISM: Artificial Sequence
<220> FEATURE:
<223> OTHER INFORMATION: GlxR_E45K

<400> SEQUENCE: 6

```
Met Glu Gly Val Gln Glu Ile Leu Ser Arg Ala Gly Ile Phe Gln Gly
1               5                   10                  15

Val Asp Pro Thr Ala Val Asn Asn Leu Ile Gln Asp Met Glu Thr Val
            20                  25                  30

Arg Phe Pro Arg Gly Ala Thr Ile Phe Asp Glu Gly Lys Pro Gly Asp
        35                  40                  45

Arg Leu Tyr Ile Ile Thr Ser Gly Lys Val Lys Leu Ala Arg His Ala
    50                  55                  60

Pro Asp Gly Arg Glu Asn Leu Leu Thr Ile Met Gly Pro Ser Asp Met
65                  70                  75                  80

Phe Gly Glu Leu Ser Ile Phe Asp Pro Gly Pro Arg Thr Ser Ser Ala
```

```
                85                  90                  95

Val Cys Val Thr Glu Val His Ala Ala Thr Met Asn Ser Asp Met Leu
            100                 105                 110

Arg Asn Trp Val Ala Asp His Pro Ala Ile Ala Glu Gln Leu Leu Arg
        115                 120                 125

Val Leu Ala Arg Arg Leu Arg Arg Thr Asn Ala Ser Leu Ala Asp Leu
    130                 135                 140

Ile Phe Thr Asp Val Pro Gly Arg Val Ala Lys Thr Leu Leu Gln Leu
145                 150                 155                 160

Ala Asn Arg Phe Gly Thr Gln Glu Ala Gly Ala Leu Arg Val Asn His
                165                 170                 175

Asp Leu Thr Gln Glu Glu Ile Ala Gln Leu Val Gly Ala Ser Arg Glu
            180                 185                 190

Thr Val Asn Lys Ala Leu Ala Thr Phe Ala His Arg Gly Trp Ile Arg
        195                 200                 205

Leu Glu Gly Lys Ser Val Leu Ile Val Asp Thr Glu His Leu Ala Arg
    210                 215                 220

Arg Ala Arg
225


<210> SEQ ID NO 7
<211> LENGTH: 227
<212> TYPE: PRT
<213> ORGANISM: Artificial Sequence
<220> FEATURE:
<223> OTHER INFORMATION: GlxR_D66A

<400> SEQUENCE: 7

Met Glu Gly Val Gln Glu Ile Leu Ser Arg Ala Gly Ile Phe Gln Gly
1               5                   10                  15

Val Asp Pro Thr Ala Val Asn Asn Leu Ile Gln Asp Met Glu Thr Val
            20                  25                  30

Arg Phe Pro Arg Gly Ala Thr Ile Phe Asp Glu Gly Glu Pro Gly Asp
        35                  40                  45

Arg Leu Tyr Ile Ile Thr Ser Gly Lys Val Lys Leu Ala Arg His Ala
    50                  55                  60

Pro Ala Gly Arg Glu Asn Leu Leu Thr Ile Met Gly Pro Ser Asp Met
65                  70                  75                  80

Phe Gly Glu Leu Ser Ile Phe Asp Pro Gly Pro Arg Thr Ser Ser Ala
                85                  90                  95

Val Cys Val Thr Glu Val His Ala Ala Thr Met Asn Ser Asp Met Leu
            100                 105                 110

Arg Asn Trp Val Ala Asp His Pro Ala Ile Ala Glu Gln Leu Leu Arg
        115                 120                 125

Val Leu Ala Arg Arg Leu Arg Arg Thr Asn Ala Ser Leu Ala Asp Leu
    130                 135                 140

Ile Phe Thr Asp Val Pro Gly Arg Val Ala Lys Thr Leu Leu Gln Leu
145                 150                 155                 160

Ala Asn Arg Phe Gly Thr Gln Glu Ala Gly Ala Leu Arg Val Asn His
                165                 170                 175

Asp Leu Thr Gln Glu Glu Ile Ala Gln Leu Val Gly Ala Ser Arg Glu
            180                 185                 190

Thr Val Asn Lys Ala Leu Ala Thr Phe Ala His Arg Gly Trp Ile Arg
        195                 200                 205

Leu Glu Gly Lys Ser Val Leu Ile Val Asp Thr Glu His Leu Ala Arg
```

```
    210                 215                 220

Arg Ala Arg
225


<210> SEQ ID NO 8
<211> LENGTH: 227
<212> TYPE: PRT
<213> ORGANISM: Artificial Sequence
<220> FEATURE:
<223> OTHER INFORMATION: GlxR_D66F

<400> SEQUENCE: 8

Met Glu Gly Val Gln Glu Ile Leu Ser Arg Ala Gly Ile Phe Gln Gly
1               5                   10                  15

Val Asp Pro Thr Ala Val Asn Asn Leu Ile Gln Asp Met Glu Thr Val
            20                  25                  30

Arg Phe Pro Arg Gly Ala Thr Ile Phe Asp Glu Gly Glu Pro Gly Asp
        35                  40                  45

Arg Leu Tyr Ile Ile Thr Ser Gly Lys Val Lys Leu Ala Arg His Ala
    50                  55                  60

Pro Phe Gly Arg Glu Asn Leu Leu Thr Ile Met Gly Pro Ser Asp Met
65                  70                  75                  80

Phe Gly Glu Leu Ser Ile Phe Asp Pro Gly Pro Arg Thr Ser Ser Ala
                85                  90                  95

Val Cys Val Thr Glu Val His Ala Ala Thr Met Asn Ser Asp Met Leu
            100                 105                 110

Arg Asn Trp Val Ala Asp His Pro Ala Ile Ala Glu Gln Leu Leu Arg
        115                 120                 125

Val Leu Ala Arg Arg Leu Arg Arg Thr Asn Ala Ser Leu Ala Asp Leu
    130                 135                 140

Ile Phe Thr Asp Val Pro Gly Arg Val Ala Lys Thr Leu Leu Gln Leu
145                 150                 155                 160

Ala Asn Arg Phe Gly Thr Gln Glu Ala Gly Ala Leu Arg Val Asn His
                165                 170                 175

Asp Leu Thr Gln Glu Glu Ile Ala Gln Leu Val Gly Ala Ser Arg Glu
            180                 185                 190

Thr Val Asn Lys Ala Leu Ala Thr Phe Ala His Arg Gly Trp Ile Arg
        195                 200                 205

Leu Glu Gly Lys Ser Val Leu Ile Val Asp Thr Glu His Leu Ala Arg
    210                 215                 220

Arg Ala Arg
225


<210> SEQ ID NO 9
<211> LENGTH: 227
<212> TYPE: PRT
<213> ORGANISM: Artificial Sequence
<220> FEATURE:
<223> OTHER INFORMATION: GlxR_D66K

<400> SEQUENCE: 9

Met Glu Gly Val Gln Glu Ile Leu Ser Arg Ala Gly Ile Phe Gln Gly
1               5                   10                  15

Val Asp Pro Thr Ala Val Asn Asn Leu Ile Gln Asp Met Glu Thr Val
            20                  25                  30

Arg Phe Pro Arg Gly Ala Thr Ile Phe Asp Glu Gly Glu Pro Gly Asp
        35                  40                  45
```

```
Arg Leu Tyr Ile Ile Thr Ser Gly Lys Val Lys Leu Ala Arg His Ala
    50                  55                  60

Pro Lys Gly Arg Glu Asn Leu Leu Thr Ile Met Gly Pro Ser Asp Met
65                  70                  75                  80

Phe Gly Glu Leu Ser Ile Phe Asp Pro Gly Pro Arg Thr Ser Ser Ala
                85                  90                  95

Val Cys Val Thr Glu Val His Ala Ala Thr Met Asn Ser Asp Met Leu
            100                 105                 110

Arg Asn Trp Val Ala Asp His Pro Ala Ile Ala Glu Gln Leu Leu Arg
        115                 120                 125

Val Leu Ala Arg Arg Leu Arg Arg Thr Asn Ala Ser Leu Ala Asp Leu
    130                 135                 140

Ile Phe Thr Asp Val Pro Gly Arg Val Ala Lys Thr Leu Leu Gln Leu
145                 150                 155                 160

Ala Asn Arg Phe Gly Thr Gln Glu Ala Gly Ala Leu Arg Val Asn His
                165                 170                 175

Asp Leu Thr Gln Glu Glu Ile Ala Gln Leu Val Gly Ala Ser Arg Glu
            180                 185                 190

Thr Val Asn Lys Ala Leu Ala Thr Phe Ala His Arg Gly Trp Ile Arg
        195                 200                 205

Leu Glu Gly Lys Ser Val Leu Ile Val Asp Thr Glu His Leu Ala Arg
    210                 215                 220

Arg Ala Arg
225


<210> SEQ ID NO 10
<211> LENGTH: 227
<212> TYPE: PRT
<213> ORGANISM: Artificial Sequence
<220> FEATURE:
<223> OTHER INFORMATION: GlxR_T166D

<400> SEQUENCE: 10

Met Glu Gly Val Gln Glu Ile Leu Ser Arg Ala Gly Ile Phe Gln Gly
1               5                   10                  15

Val Asp Pro Thr Ala Val Asn Asn Leu Ile Gln Asp Met Glu Thr Val
            20                  25                  30

Arg Phe Pro Arg Gly Ala Thr Ile Phe Asp Glu Gly Glu Pro Gly Asp
        35                  40                  45

Arg Leu Tyr Ile Ile Thr Ser Gly Lys Val Lys Leu Ala Arg His Ala
    50                  55                  60

Pro Asp Gly Arg Glu Asn Leu Leu Thr Ile Met Gly Pro Ser Asp Met
65                  70                  75                  80

Phe Gly Glu Leu Ser Ile Phe Asp Pro Gly Pro Arg Thr Ser Ser Ala
                85                  90                  95

Val Cys Val Thr Glu Val His Ala Ala Thr Met Asn Ser Asp Met Leu
            100                 105                 110

Arg Asn Trp Val Ala Asp His Pro Ala Ile Ala Glu Gln Leu Leu Arg
        115                 120                 125

Val Leu Ala Arg Arg Leu Arg Arg Thr Asn Ala Ser Leu Ala Asp Leu
    130                 135                 140

Ile Phe Thr Asp Val Pro Gly Arg Val Ala Lys Thr Leu Leu Gln Leu
145                 150                 155                 160

Ala Asn Arg Phe Gly Asp Gln Glu Ala Gly Ala Leu Arg Val Asn His
                165                 170                 175
```

```
Asp Leu Thr Gln Glu Glu Ile Ala Gln Leu Val Gly Ala Ser Arg Glu
            180                 185                 190

Thr Val Asn Lys Ala Leu Ala Thr Phe Ala His Arg Gly Trp Ile Arg
        195                 200                 205

Leu Glu Gly Lys Ser Val Leu Ile Val Asp Thr Glu His Leu Ala Arg
    210                 215                 220

Arg Ala Arg
225


<210> SEQ ID NO 11
<211> LENGTH: 227
<212> TYPE: PRT
<213> ORGANISM: Artificial Sequence
<220> FEATURE:
<223> OTHER INFORMATION: GlxR_T166F

<400> SEQUENCE: 11

Met Glu Gly Val Gln Glu Ile Leu Ser Arg Ala Gly Ile Phe Gln Gly
1               5                   10                  15

Val Asp Pro Thr Ala Val Asn Asn Leu Ile Gln Asp Met Glu Thr Val
            20                  25                  30

Arg Phe Pro Arg Gly Ala Thr Ile Phe Asp Glu Gly Glu Pro Gly Asp
        35                  40                  45

Arg Leu Tyr Ile Ile Thr Ser Gly Lys Val Lys Leu Ala Arg His Ala
    50                  55                  60

Pro Asp Gly Arg Glu Asn Leu Leu Thr Ile Met Gly Pro Ser Asp Met
65                  70                  75                  80

Phe Gly Glu Leu Ser Ile Phe Asp Pro Gly Pro Arg Thr Ser Ser Ala
                85                  90                  95

Val Cys Val Thr Glu Val His Ala Ala Thr Met Asn Ser Asp Met Leu
            100                 105                 110

Arg Asn Trp Val Ala Asp His Pro Ala Ile Ala Glu Gln Leu Leu Arg
        115                 120                 125

Val Leu Ala Arg Arg Leu Arg Arg Thr Asn Ala Ser Leu Ala Asp Leu
    130                 135                 140

Ile Phe Thr Asp Val Pro Gly Arg Val Ala Lys Thr Leu Leu Gln Leu
145                 150                 155                 160

Ala Asn Arg Phe Gly Phe Gln Glu Ala Gly Ala Leu Arg Val Asn His
                165                 170                 175

Asp Leu Thr Gln Glu Glu Ile Ala Gln Leu Val Gly Ala Ser Arg Glu
            180                 185                 190

Thr Val Asn Lys Ala Leu Ala Thr Phe Ala His Arg Gly Trp Ile Arg
        195                 200                 205

Leu Glu Gly Lys Ser Val Leu Ile Val Asp Thr Glu His Leu Ala Arg
    210                 215                 220

Arg Ala Arg
225


<210> SEQ ID NO 12
<211> LENGTH: 227
<212> TYPE: PRT
<213> ORGANISM: Artificial Sequence
<220> FEATURE:
<223> OTHER INFORMATION: GlxR_T166K

<400> SEQUENCE: 12

Met Glu Gly Val Gln Glu Ile Leu Ser Arg Ala Gly Ile Phe Gln Gly
1               5                   10                  15
```

```
Val Asp Pro Thr Ala Val Asn Asn Leu Ile Gln Asp Met Glu Thr Val
            20                  25                  30

Arg Phe Pro Arg Gly Ala Thr Ile Phe Asp Glu Gly Glu Pro Gly Asp
        35                  40                  45

Arg Leu Tyr Ile Ile Thr Ser Gly Lys Val Lys Leu Ala Arg His Ala
    50                  55                  60

Pro Asp Gly Arg Glu Asn Leu Leu Thr Ile Met Gly Pro Ser Asp Met
65                  70                  75                  80

Phe Gly Glu Leu Ser Ile Phe Asp Pro Gly Pro Arg Thr Ser Ser Ala
                85                  90                  95

Val Cys Val Thr Glu Val His Ala Ala Thr Met Asn Ser Asp Met Leu
            100                 105                 110

Arg Asn Trp Val Ala Asp His Pro Ala Ile Ala Glu Gln Leu Leu Arg
        115                 120                 125

Val Leu Ala Arg Arg Leu Arg Arg Thr Asn Ala Ser Leu Ala Asp Leu
    130                 135                 140

Ile Phe Thr Asp Val Pro Gly Arg Val Ala Lys Thr Leu Leu Gln Leu
145                 150                 155                 160

Ala Asn Arg Phe Gly Lys Gln Glu Ala Gly Ala Leu Arg Val Asn His
                165                 170                 175

Asp Leu Thr Gln Glu Glu Ile Ala Gln Leu Val Gly Ala Ser Arg Glu
            180                 185                 190

Thr Val Asn Lys Ala Leu Ala Thr Phe Ala His Arg Gly Trp Ile Arg
        195                 200                 205

Leu Glu Gly Lys Ser Val Leu Ile Val Asp Thr Glu His Leu Ala Arg
    210                 215                 220

Arg Ala Arg
225


<210> SEQ ID NO 13
<211> LENGTH: 227
<212> TYPE: PRT
<213> ORGANISM: Artificial Sequence
<220> FEATURE:
<223> OTHER INFORMATION: GlxR_E168A

<400> SEQUENCE: 13

Met Glu Gly Val Gln Glu Ile Leu Ser Arg Ala Gly Ile Phe Gln Gly
1               5                   10                  15

Val Asp Pro Thr Ala Val Asn Asn Leu Ile Gln Asp Met Glu Thr Val
            20                  25                  30

Arg Phe Pro Arg Gly Ala Thr Ile Phe Asp Glu Gly Glu Pro Gly Asp
        35                  40                  45

Arg Leu Tyr Ile Ile Thr Ser Gly Lys Val Lys Leu Ala Arg His Ala
    50                  55                  60

Pro Asp Gly Arg Glu Asn Leu Leu Thr Ile Met Gly Pro Ser Asp Met
65                  70                  75                  80

Phe Gly Glu Leu Ser Ile Phe Asp Pro Gly Pro Arg Thr Ser Ser Ala
                85                  90                  95

Val Cys Val Thr Glu Val His Ala Ala Thr Met Asn Ser Asp Met Leu
            100                 105                 110

Arg Asn Trp Val Ala Asp His Pro Ala Ile Ala Glu Gln Leu Leu Arg
        115                 120                 125

Val Leu Ala Arg Arg Leu Arg Arg Thr Asn Ala Ser Leu Ala Asp Leu
    130                 135                 140
```

```
Ile Phe Thr Asp Val Pro Gly Arg Val Ala Lys Thr Leu Leu Gln Leu
145                 150                 155                 160

Ala Asn Arg Phe Gly Thr Gln Ala Ala Gly Ala Leu Arg Val Asn His
                165                 170                 175

Asp Leu Thr Gln Glu Glu Ile Ala Gln Leu Val Gly Ala Ser Arg Glu
            180                 185                 190

Thr Val Asn Lys Ala Leu Ala Thr Phe Ala His Arg Gly Trp Ile Arg
        195                 200                 205

Leu Glu Gly Lys Ser Val Leu Ile Val Asp Thr Glu His Leu Ala Arg
    210                 215                 220

Arg Ala Arg
225


<210> SEQ ID NO 14
<211> LENGTH: 227
<212> TYPE: PRT
<213> ORGANISM: Artificial Sequence
<220> FEATURE:
<223> OTHER INFORMATION: GlxR_E168F

<400> SEQUENCE: 14

Met Glu Gly Val Gln Glu Ile Leu Ser Arg Ala Gly Ile Phe Gln Gly
1               5                   10                  15

Val Asp Pro Thr Ala Val Asn Asn Leu Ile Gln Asp Met Glu Thr Val
            20                  25                  30

Arg Phe Pro Arg Gly Ala Thr Ile Phe Asp Glu Gly Glu Pro Gly Asp
        35                  40                  45

Arg Leu Tyr Ile Ile Thr Ser Gly Lys Val Lys Leu Ala Arg His Ala
    50                  55                  60

Pro Asp Gly Arg Glu Asn Leu Leu Thr Ile Met Gly Pro Ser Asp Met
65                  70                  75                  80

Phe Gly Glu Leu Ser Ile Phe Asp Pro Gly Pro Arg Thr Ser Ser Ala
                85                  90                  95

Val Cys Val Thr Glu Val His Ala Ala Thr Met Asn Ser Asp Met Leu
            100                 105                 110

Arg Asn Trp Val Ala Asp His Pro Ala Ile Ala Glu Gln Leu Leu Arg
        115                 120                 125

Val Leu Ala Arg Arg Leu Arg Arg Thr Asn Ala Ser Leu Ala Asp Leu
    130                 135                 140

Ile Phe Thr Asp Val Pro Gly Arg Val Ala Lys Thr Leu Leu Gln Leu
145                 150                 155                 160

Ala Asn Arg Phe Gly Thr Gln Phe Ala Gly Ala Leu Arg Val Asn His
                165                 170                 175

Asp Leu Thr Gln Glu Glu Ile Ala Gln Leu Val Gly Ala Ser Arg Glu
            180                 185                 190

Thr Val Asn Lys Ala Leu Ala Thr Phe Ala His Arg Gly Trp Ile Arg
        195                 200                 205

Leu Glu Gly Lys Ser Val Leu Ile Val Asp Thr Glu His Leu Ala Arg
    210                 215                 220

Arg Ala Arg
225


<210> SEQ ID NO 15
<211> LENGTH: 227
<212> TYPE: PRT
<213> ORGANISM: Artificial Sequence
```

<220> FEATURE:
<223> OTHER INFORMATION: GlxR_E168K

<400> SEQUENCE: 15

```
Met Glu Gly Val Gln Glu Ile Leu Ser Arg Ala Gly Ile Phe Gln Gly
1               5                   10                  15

Val Asp Pro Thr Ala Val Asn Asn Leu Ile Gln Asp Met Glu Thr Val
            20                  25                  30

Arg Phe Pro Arg Gly Ala Thr Ile Phe Asp Glu Gly Glu Pro Gly Asp
        35                  40                  45

Arg Leu Tyr Ile Ile Thr Ser Gly Lys Val Lys Leu Ala Arg His Ala
    50                  55                  60

Pro Asp Gly Arg Glu Asn Leu Leu Thr Ile Met Gly Pro Ser Asp Met
65                  70                  75                  80

Phe Gly Glu Leu Ser Ile Phe Asp Pro Gly Pro Arg Thr Ser Ser Ala
                85                  90                  95

Val Cys Val Thr Glu Val His Ala Ala Thr Met Asn Ser Asp Met Leu
            100                 105                 110

Arg Asn Trp Val Ala Asp His Pro Ala Ile Ala Glu Gln Leu Leu Arg
        115                 120                 125

Val Leu Ala Arg Arg Leu Arg Arg Thr Asn Ala Ser Leu Ala Asp Leu
    130                 135                 140

Ile Phe Thr Asp Val Pro Gly Arg Val Ala Lys Thr Leu Leu Gln Leu
145                 150                 155                 160

Ala Asn Arg Phe Gly Thr Gln Lys Ala Gly Ala Leu Arg Val Asn His
                165                 170                 175

Asp Leu Thr Gln Glu Glu Ile Ala Gln Leu Val Gly Ala Ser Arg Glu
            180                 185                 190

Thr Val Asn Lys Ala Leu Ala Thr Phe Ala His Arg Gly Trp Ile Arg
        195                 200                 205

Leu Glu Gly Lys Ser Val Leu Ile Val Asp Thr Glu His Leu Ala Arg
    210                 215                 220

Arg Ala Arg
225
```

<210> SEQ ID NO 16
<211> LENGTH: 35
<212> TYPE: DNA
<213> ORGANISM: Artificial Sequence
<220> FEATURE:
<223> OTHER INFORMATION: glxR L1

<400> SEQUENCE: 16

```
gaattcgagc tcggtaccct gagaccccac gcgag                                35
```

<210> SEQ ID NO 17
<211> LENGTH: 36
<212> TYPE: DNA
<213> ORGANISM: Artificial Sequence
<220> FEATURE:
<223> OTHER INFORMATION: glxR R2

<400> SEQUENCE: 17

```
gactctagag gatccccatc gacggtgtca ccccac                               36
```

<210> SEQ ID NO 18
<211> LENGTH: 38
<212> TYPE: DNA
<213> ORGANISM: Artificial Sequence
<220> FEATURE:
<223> OTHER INFORMATION: glxR(E45A) L2

<400> SEQUENCE: 18
gtaaaggcgg tcacctggcg cgccctcgtc gaagatgg 38

<210> SEQ ID NO 19
<211> LENGTH: 38
<212> TYPE: DNA
<213> ORGANISM: Artificial Sequence
<220> FEATURE:
<223> OTHER INFORMATION: glxR(E45A) R1

<400> SEQUENCE: 19
ccatcttcga cgagggcgcg ccaggtgacc gcctttac 38

<210> SEQ ID NO 20
<211> LENGTH: 21
<212> TYPE: DNA
<213> ORGANISM: Artificial Sequence
<220> FEATURE:
<223> OTHER INFORMATION: pDZ_F (pDZ vector sequencing primer_forward)

<400> SEQUENCE: 20
tattacgcca gctggcgaaa g 21

<210> SEQ ID NO 21
<211> LENGTH: 21
<212> TYPE: DNA
<213> ORGANISM: Artificial Sequence
<220> FEATURE:
<223> OTHER INFORMATION: pDZ_R (pDZ vector sequencing primer_reverse)

<400> SEQUENCE: 21
ttccggctcg tatgttgtgt g 21

<210> SEQ ID NO 22
<211> LENGTH: 38
<212> TYPE: DNA
<213> ORGANISM: Artificial Sequence
<220> FEATURE:
<223> OTHER INFORMATION: glxR(E45S) L2

<400> SEQUENCE: 22
gtaaaggcgg tcacctggag agccctcgtc gaagatgg 38

<210> SEQ ID NO 23
<211> LENGTH: 38
<212> TYPE: DNA
<213> ORGANISM: Artificial Sequence
<220> FEATURE:
<223> OTHER INFORMATION: glxR(E45S) R1

<400> SEQUENCE: 23
ccatcttcga cgagggctct ccaggtgacc gcctttac 38

<210> SEQ ID NO 24
<211> LENGTH: 38
<212> TYPE: DNA
<213> ORGANISM: Artificial Sequence
<220> FEATURE:
<223> OTHER INFORMATION: glxR(E45F) L2

<400> SEQUENCE: 24
gtaaaggcgg tcacctggaa agccctcgtc gaagatgg 38

<210> SEQ ID NO 25
<211> LENGTH: 38
<212> TYPE: DNA
<213> ORGANISM: Artificial Sequence
<220> FEATURE:
<223> OTHER INFORMATION: glxR(E45F) R1

<400> SEQUENCE: 25
ccatcttcga cgagggcttt ccaggtgacc gcctttac 38

<210> SEQ ID NO 26
<211> LENGTH: 38
<212> TYPE: DNA
<213> ORGANISM: Artificial Sequence
<220> FEATURE:
<223> OTHER INFORMATION: glxR(E45K) L2

<400> SEQUENCE: 26
gtaaaggcgg tcacctggct tgccctcgtc gaagatgg 38

<210> SEQ ID NO 27
<211> LENGTH: 38
<212> TYPE: DNA
<213> ORGANISM: Artificial Sequence
<220> FEATURE:
<223> OTHER INFORMATION: glxR(E45K) R1

<400> SEQUENCE: 27
ccatcttcga cgagggcaag ccaggtgacc gcctttac 38

<210> SEQ ID NO 28
<211> LENGTH: 34
<212> TYPE: DNA
<213> ORGANISM: Artificial Sequence
<220> FEATURE:
<223> OTHER INFORMATION: glxR(D66A) L2

<400> SEQUENCE: 28
ggttttcgcg gcctgccggt gcgtggcgcg caag 34

<210> SEQ ID NO 29
<211> LENGTH: 34
<212> TYPE: DNA
<213> ORGANISM: Artificial Sequence
<220> FEATURE:
<223> OTHER INFORMATION: glxR(D66A) R1

<400> SEQUENCE: 29
gcgccacgca ccggcaggcc gcgaaaacct gctg 34

<210> SEQ ID NO 30
<211> LENGTH: 34
<212> TYPE: DNA
<213> ORGANISM: Artificial Sequence
<220> FEATURE:
<223> OTHER INFORMATION: glxR(D66F) L2

<400> SEQUENCE: 30
cagcaggttt tcgcggccaa acggtgcgtg gcgc 34

<210> SEQ ID NO 31
<211> LENGTH: 34
<212> TYPE: DNA
<213> ORGANISM: Artificial Sequence
<220> FEATURE:
<223> OTHER INFORMATION: glxR(D66F) R1

<400> SEQUENCE: 31
gcgccacgca ccgtttggcc gcgaaaacct gctg 34

<210> SEQ ID NO 32
<211> LENGTH: 35
<212> TYPE: DNA
<213> ORGANISM: Artificial Sequence
<220> FEATURE:
<223> OTHER INFORMATION: glxR(D66K) L2

<400> SEQUENCE: 32
ggttttcgcg gcctttccgg tgcgtggcgc gcaag 35

<210> SEQ ID NO 33
<211> LENGTH: 34
<212> TYPE: DNA
<213> ORGANISM: Artificial Sequence
<220> FEATURE:
<223> OTHER INFORMATION: glxR(D66K) R1

<400> SEQUENCE: 33
gcgccacgca ccgaaaggcc gcgaaaacct gctg 34

<210> SEQ ID NO 34
<211> LENGTH: 34
<212> TYPE: DNA
<213> ORGANISM: Artificial Sequence
<220> FEATURE:
<223> OTHER INFORMATION: glxR(T166D) L2

<400> SEQUENCE: 34
gccagcttct tggtcgccga agcggttagc cagc 34

<210> SEQ ID NO 35
<211> LENGTH: 33
<212> TYPE: DNA
<213> ORGANISM: Artificial Sequence
<220> FEATURE:
<223> OTHER INFORMATION: glxR(T166D) R1

<400> SEQUENCE: 35
aaccgcttcg gcgaccaaga agctggcgcg ctg 33

<210> SEQ ID NO 36
<211> LENGTH: 34
<212> TYPE: DNA
<213> ORGANISM: Artificial Sequence
<220> FEATURE:
<223> OTHER INFORMATION: glxR(T166F) L2

<400> SEQUENCE: 36
gccagcttct tggaagccga agcggttagc cagc 34

<210> SEQ ID NO 37
<211> LENGTH: 33
<212> TYPE: DNA
<213> ORGANISM: Artificial Sequence
<220> FEATURE:
<223> OTHER INFORMATION: glxR(T166F) R1

<400> SEQUENCE: 37
aaccgcttcg gcttccaaga agctggcgcg ctg 33

<210> SEQ ID NO 38

<211> LENGTH: 34
<212> TYPE: DNA
<213> ORGANISM: Artificial Sequence
<220> FEATURE:
<223> OTHER INFORMATION: glxR(T166K) L2

<400> SEQUENCE: 38
gccagcttct tgtttgccga agcggttagc cagc 34

<210> SEQ ID NO 39
<211> LENGTH: 33
<212> TYPE: DNA
<213> ORGANISM: Artificial Sequence
<220> FEATURE:
<223> OTHER INFORMATION: glxR(T166K) R1

<400> SEQUENCE: 39
aaccgcttcg gcaaacaaga agctggcgcg ctg 33

<210> SEQ ID NO 40
<211> LENGTH: 34
<212> TYPE: DNA
<213> ORGANISM: Artificial Sequence
<220> FEATURE:
<223> OTHER INFORMATION: glxR(E168A) L2

<400> SEQUENCE: 40
agcgcgccag cagcttgggc gccgaagcgg ttag 34

<210> SEQ ID NO 41
<211> LENGTH: 34
<212> TYPE: DNA
<213> ORGANISM: Artificial Sequence
<220> FEATURE:
<223> OTHER INFORMATION: glxR(E168A) R1

<400> SEQUENCE: 41
cttcggcgcc caagctgctg gcgcgctgcg cgtg 34

<210> SEQ ID NO 42
<211> LENGTH: 34
<212> TYPE: DNA
<213> ORGANISM: Artificial Sequence
<220> FEATURE:
<223> OTHER INFORMATION: glxR(E168F) L2

<400> SEQUENCE: 42
agcgcgccag caaattgggc gccgaagcgg ttag 34

<210> SEQ ID NO 43
<211> LENGTH: 34
<212> TYPE: DNA
<213> ORGANISM: Artificial Sequence
<220> FEATURE:
<223> OTHER INFORMATION: glxR(E168F) R1

<400> SEQUENCE: 43
cttcggcgcc caatttgctg gcgcgctgcg cgtg 34

<210> SEQ ID NO 44
<211> LENGTH: 34
<212> TYPE: DNA
<213> ORGANISM: Artificial Sequence
<220> FEATURE:
<223> OTHER INFORMATION: glxR(E168K) L2

<400> SEQUENCE: 44
agcgcgccag ccttttgggc gccgaagcgg ttag 34

<210> SEQ ID NO 45
<211> LENGTH: 34
<212> TYPE: DNA
<213> ORGANISM: Artificial Sequence
<220> FEATURE:
<223> OTHER INFORMATION: glxR(E168K) R1

<400> SEQUENCE: 45
cttcggcgcc caaaaggctg gcgcgctgcg cgtg 34

<210> SEQ ID NO 46
<211> LENGTH: 421
<212> TYPE: PRT
<213> ORGANISM: Artificial Sequence
<220> FEATURE:
<223> OTHER INFORMATION: LysC_L377K

<400> SEQUENCE: 46

Met Ala Leu Val Val Gln Lys Tyr Gly Gly Ser Ser Leu Glu Ser Ala
1 5 10 15

Glu Arg Ile Arg Asn Val Ala Glu Arg Ile Val Ala Thr Lys Lys Ala
20 25 30

Gly Asn Asp Val Val Val Val Cys Ser Ala Met Gly Asp Thr Thr Asp
35 40 45

Glu Leu Leu Glu Leu Ala Ala Ala Val Asn Pro Val Pro Pro Ala Arg
50 55 60

Glu Met Asp Met Leu Leu Thr Ala Gly Glu Arg Ile Ser Asn Ala Leu
65 70 75 80

Val Ala Met Ala Ile Glu Ser Leu Gly Ala Glu Ala Gln Ser Phe Thr
85 90 95

Gly Ser Gln Ala Gly Val Leu Thr Thr Glu Arg His Gly Asn Ala Arg
100 105 110

Ile Val Asp Val Thr Pro Gly Arg Val Arg Glu Ala Leu Asp Glu Gly
115 120 125

Lys Ile Cys Ile Val Ala Gly Phe Gln Gly Val Asn Lys Glu Thr Arg
130 135 140

Asp Val Thr Thr Leu Gly Arg Gly Gly Ser Asp Thr Thr Ala Val Ala
145 150 155 160

Leu Ala Ala Ala Leu Asn Ala Asp Val Cys Glu Ile Tyr Ser Asp Val
165 170 175

Asp Gly Val Tyr Thr Ala Asp Pro Arg Ile Val Pro Asn Ala Gln Lys
180 185 190

Leu Glu Lys Leu Ser Phe Glu Glu Met Leu Glu Leu Ala Ala Val Gly
195 200 205

Ser Lys Ile Leu Val Leu Arg Ser Val Glu Tyr Ala Arg Ala Phe Asn
210 215 220

Val Pro Leu Arg Val Arg Ser Ser Tyr Ser Asn Asp Pro Gly Thr Leu
225 230 235 240

Ile Ala Gly Ser Met Glu Asp Ile Pro Val Glu Glu Ala Val Leu Thr
245 250 255

Gly Val Ala Thr Asp Lys Ser Glu Ala Lys Val Thr Val Leu Gly Ile
260 265 270

Ser Asp Lys Pro Gly Glu Ala Ala Lys Val Phe Arg Ala Leu Ala Asp
275 280 285

```
Ala Glu Ile Asn Ile Asp Met Val Leu Gln Asn Val Ser Ser Val Glu
    290                 295                 300

Asp Gly Thr Thr Asp Ile Thr Phe Thr Cys Pro Arg Ser Asp Gly Arg
305                 310                 315                 320

Arg Ala Met Glu Ile Leu Lys Lys Leu Gln Val Gln Gly Asn Trp Thr
                325                 330                 335

Asn Val Leu Tyr Asp Asp Gln Val Gly Lys Val Ser Leu Val Gly Ala
            340                 345                 350

Gly Met Lys Ser His Pro Gly Val Thr Ala Glu Phe Met Glu Ala Leu
        355                 360                 365

Arg Asp Val Asn Val Asn Ile Glu Lys Ile Ser Thr Ser Glu Ile Arg
    370                 375                 380

Ile Ser Val Leu Ile Arg Glu Asp Asp Leu Asp Ala Ala Ala Arg Ala
385                 390                 395                 400

Leu His Glu Gln Phe Gln Leu Gly Gly Glu Asp Glu Ala Val Val Tyr
                405                 410                 415

Ala Gly Thr Gly Arg
            420


<210> SEQ ID NO 47
<211> LENGTH: 34
<212> TYPE: DNA
<213> ORGANISM: Artificial Sequence
<220> FEATURE:
<223> OTHER INFORMATION: lysC L1

<400> SEQUENCE: 47

tcgagctcgg tacccgctgc gcagtgttga atac                                34


<210> SEQ ID NO 48
<211> LENGTH: 34
<212> TYPE: DNA
<213> ORGANISM: Artificial Sequence
<220> FEATURE:
<223> OTHER INFORMATION: lysC R2

<400> SEQUENCE: 48

ctctagagga tccccgttca cctcagagac gatt                                34


<210> SEQ ID NO 49
<211> LENGTH: 30
<212> TYPE: DNA
<213> ORGANISM: Artificial Sequence
<220> FEATURE:
<223> OTHER INFORMATION: lysC(L377K) L2

<400> SEQUENCE: 49

tggaaatctt ttcgatgttc acgttgacat                                     30


<210> SEQ ID NO 50
<211> LENGTH: 30
<212> TYPE: DNA
<213> ORGANISM: Artificial Sequence
<220> FEATURE:
<223> OTHER INFORMATION: lysC(L377K) R1

<400> SEQUENCE: 50

atgtcaacgt gaacatcgaa aagatttcca                                     30


<210> SEQ ID NO 51
<211> LENGTH: 445
<212> TYPE: PRT
```

```
<213> ORGANISM: Artificial Sequence
<220> FEATURE:
<223> OTHER INFORMATION: Hom_R407H

<400> SEQUENCE: 51

Met Thr Ser Ala Ser Ala Pro Ser Phe Asn Pro Gly Lys Gly Pro Gly
1               5                   10                  15

Ser Ala Val Gly Ile Ala Leu Leu Gly Phe Gly Thr Val Gly Thr Glu
            20                  25                  30

Val Met Arg Leu Met Thr Glu Tyr Gly Asp Glu Leu Ala His Arg Ile
        35                  40                  45

Gly Gly Pro Leu Glu Val Arg Gly Ile Ala Val Ser Asp Ile Ser Lys
    50                  55                  60

Pro Arg Glu Gly Val Ala Pro Glu Leu Leu Thr Glu Asp Ala Phe Ala
65                  70                  75                  80

Leu Ile Glu Arg Glu Asp Val Asp Ile Val Val Glu Val Ile Gly Gly
                85                  90                  95

Ile Glu Tyr Pro Arg Glu Val Val Leu Ala Ala Leu Lys Ala Gly Lys
            100                 105                 110

Ser Val Val Thr Ala Asn Lys Ala Leu Val Ala Ala His Ser Ala Glu
        115                 120                 125

Leu Ala Asp Ala Ala Glu Ala Ala Asn Val Asp Leu Tyr Phe Glu Ala
    130                 135                 140

Ala Val Ala Gly Ala Ile Pro Val Val Gly Pro Leu Arg Arg Ser Leu
145                 150                 155                 160

Ala Gly Asp Gln Ile Gln Ser Val Met Gly Ile Val Asn Gly Thr Thr
                165                 170                 175

Asn Phe Ile Leu Asp Ala Met Asp Ser Thr Gly Ala Asp Tyr Ala Asp
            180                 185                 190

Ser Leu Ala Glu Ala Thr Arg Leu Gly Tyr Ala Glu Ala Asp Pro Thr
        195                 200                 205

Ala Asp Val Glu Gly His Asp Ala Ala Ser Lys Ala Ala Ile Leu Ala
    210                 215                 220

Ser Ile Ala Phe His Thr Arg Val Thr Ala Asp Asp Val Tyr Cys Glu
225                 230                 235                 240

Gly Ile Ser Asn Ile Ser Ala Ala Asp Ile Glu Ala Ala Gln Gln Ala
                245                 250                 255

Gly His Thr Ile Lys Leu Leu Ala Ile Cys Glu Lys Phe Thr Asn Lys
            260                 265                 270

Glu Gly Lys Ser Ala Ile Ser Ala Arg Val His Pro Thr Leu Leu Pro
        275                 280                 285

Val Ser His Pro Leu Ala Ser Val Asn Lys Ser Phe Asn Ala Ile Phe
    290                 295                 300

Val Glu Ala Glu Ala Ala Gly Arg Leu Met Phe Tyr Gly Asn Gly Ala
305                 310                 315                 320

Gly Gly Ala Pro Thr Ala Ser Ala Val Leu Gly Asp Val Val Gly Ala
                325                 330                 335

Ala Arg Asn Lys Val His Gly Gly Arg Ala Pro Gly Glu Ser Thr Tyr
            340                 345                 350

Ala Asn Leu Pro Ile Ala Asp Phe Gly Glu Thr Thr Thr Arg Tyr His
        355                 360                 365

Leu Asp Met Asp Val Glu Asp Arg Val Gly Val Leu Ala Glu Leu Ala
    370                 375                 380

Ser Leu Phe Ser Glu Gln Gly Ile Ser Leu Arg Thr Ile Arg Gln Glu
```

-continued

```
385                 390                 395                 400

Glu Arg Asp Asp Asp Ala His Leu Ile Val Val Thr His Ser Ala Leu
                405                 410                 415

Glu Ser Asp Leu Ser Arg Thr Val Glu Leu Leu Lys Ala Lys Pro Val
            420                 425                 430

Val Lys Ala Ile Asn Ser Val Ile Arg Leu Glu Arg Asp
        435                 440                 445


<210> SEQ ID NO 52
<211> LENGTH: 34
<212> TYPE: DNA
<213> ORGANISM: Artificial Sequence
<220> FEATURE:
<223> OTHER INFORMATION: hom L1

<400> SEQUENCE: 52

atcctctaga gtcgacccaa ctgcagacgt cgaa                              34


<210> SEQ ID NO 53
<211> LENGTH: 35
<212> TYPE: DNA
<213> ORGANISM: Artificial Sequence
<220> FEATURE:
<223> OTHER INFORMATION: hom R2

<400> SEQUENCE: 53

atgcctgcag gtcgacatag acagatttgt ccacg                             35


<210> SEQ ID NO 54
<211> LENGTH: 35
<212> TYPE: DNA
<213> ORGANISM: Artificial Sequence
<220> FEATURE:
<223> OTHER INFORMATION: hom(R407H) L2

<400> SEQUENCE: 54

gtgaccacga tcagatgtgc atcatcatcg cgctc                             35


<210> SEQ ID NO 55
<211> LENGTH: 35
<212> TYPE: DNA
<213> ORGANISM: Artificial Sequence
<220> FEATURE:
<223> OTHER INFORMATION: hom(R407H) R1

<400> SEQUENCE: 55

gcgatgatga tgcacatctg atcgtggtca cccac                             35
```

GlxR PROTEIN VARIANT OR THREONINE PRODUCTION METHOD USING SAME

CROSS-REFERENCE TO RELATED APPLICATION(S)

A computer readable text file, entitled "133660-03-8010-US_Sequence_Listing_ST25.txt," created on or about Jun. 5, 2024, with a file size of 44,590 bytes contains the sequence listing for this application and is hereby incorporated by reference in its entirety.

TECHNICAL FIELD

The present application claims the benefit of the priority based on Korean Patent Application No. 10-2021-0003609 filed on Jan. 11, 2021, and the entire contents of the document of the corresponding Korean patent application are incorporated as a part of the present description.

The present application relates to a GlxR protein variant or a threonine production method using the same.

BACKGROUND ART

L-threonine is an essential amino acid, and is used as a feed or food additive, a synthetic raw material for pharmaceuticals and an infusion solution for medicine. L-threonine is mainly produced by microbial fermentation technology, and for example, it may be produced using an *Escherichia, Corynebacterium, Serratia*, or *Providencia* sp. microorganism.

Recently, many attempts have been made to improve a preparation method of L-threonine using a *Corynebacterium* sp. strain. As gene recombination technology develops, technologies for development of more improved L-threonine producing strains have been reported by introducing site-specific gene substitution, gene amplification and deletion, and the like for a L-threonine producing strain developed by random mutagenesis. In addition, there is also an attempt to introduce a foreign gene from other bacteria.

Despite these efforts, development of a technology for improving the productivity of useful substances such as L-threonine is still required.

PRIOR ART

Patent Document (Patent document 1) U.S. Patent Publication No. 2016-0369310

DISCLOSURE

Technical Problem

One example provides a novel GlxR protein variant. The GlxR protein variant may be a polypeptide in which an amino acid at a position of one or more selected from the group consisting of the $45^{th}$, $66^{th}$, $166^{th}$ and $168^{th}$ from the N-terminus in the amino acid sequence of SEQ ID NO: 1 and/or corresponding thereto (at one or more positions selected above) is substituted with other amino acid. The polypeptide may have the function of a major transcriptional regulator regulating a metabolic process.

Another example provides a polynucleotide encoding the GlxR protein variant.

Other example provides a vector comprising the polynucleotide.

Other example provides a microorganism comprising the GlxR protein variant, the polynucleotide, a vector comprising the polynucleotide, or a combination thereof.

Other example provides a production method of threonine comprising culturing the microorganism in a medium.

The microorganism may be a *Corynebacterium* sp. microorganism.

Technical Solution

One example provided in the present application provides a technology related to developing a strain with improved (increased) production of threonine by improving GlxR protein and/org GlxR gene encoding this. In one example, the threonine may be L-threonine.

One aspect of the present application to achieve the purpose may provide a GlxR protein variant, in which an amino acid residue at a position of one or more selected from the group consisting of the $45^{th}$, $66^{th}$, $166^{th}$ and $168^{th}$ from the N-terminus in the amino acid sequence of GlxR protein and/or corresponding position thereto is substituted with other kind of amino acid residue.

Herein, "GlxR (CRP-like cyclic AMP-dependent global transcriptional regulator, for example, Cg0350)" may mean a global regulator which involves in not only carbon metabolism but also various cell functions to regulate various genes, and for example, it may regulate expression of a gene encoding glyoxylic acid bypass enzymes, isocitrate lyase and/or malate synthase (for example, aceA (cg2560) and aceB (cg2559)).

The GlxR protein may comprise the amino acid sequence of SEQ ID NO: 1 or consist of the amino acid sequence of SEQ ID NO: 1, and the gIxR gene encoding the GlxR protein may comprise the nucleic acid sequence of SEQ ID NO: 2 or consist of the nucleic acid sequence of SEQ ID NO: 2. The amino acid sequence of SEQ ID NO: 1 and the nucleic acid sequence of SEQ ID NO: 2 were described in Table 1 below.

The amino acid sequence of the GlxR protein and the nucleotide sequence (nucleic acid sequence) of the gene encoding the GlxR protein (for example, gIxR) were easily obtained from database known in the art such as U.S. National Center for Biotechnology Information (NCBI) and Japanese DNA databank (DDBJ), and for example, it may be GenBank Accession No. WP_003855810.1.

TABLE 1

| Name | Sequence | SEQ ID NO |
|---|---|---|
| GlxR_amino acid | MEGVQEILSRAGIFQGVDPTAVNNLIQDMETVRFPRGA TIFDEGEPGDRLYIITSGKVKLARHAPDGRENLLTIMGP SDMFGELSIFDPGPRTSSAVCVTEVHAATMNSDMLRN WVADHPAIAEQLLRVLARRLRRTNASLADLIFTDVPGR VAKTLLQLANRFGTQEAGALRVNHDLTQEEIAQLVGAS RETVNKALATFAHRGWIRLEGKSVLIVDTEHLARRAR | SEQ ID NO: 1 |

TABLE 1-continued

| Name | Sequence | SEQ ID NO |
|---|---|---|
| glxR_nucleic acid | GTGGAAGGTGTACAGGAGATCCTGTCGCGCGCCGG AATTTTTCAAGGCGTTGACCCAACGGCAGTCAATAA CCTCATCCAGGATATGGAGACCGTTCGCTTCCCACG CGGAGCAACCATCTTCGACGAGGGCGAGCCAGGTG ACCGCCTTTACATCATCACCTCCGGCAAAGTGAAGC TTGCGCGCCACGCACCGGACGGCCGCGAAAACCTG CTGACCATCATGGGTCCTTCCGACATGTTCGGTGAG CTCTCCATCTTCGACCCAGGCCCACGCACCTCCTCT GCAGTGTGTGTCACCGAAGTTCATGCAGCAACCATG AACTCTGACATGCTGCGCAACTGGGTAGCTGACCAC CCAGCTATCGCTGAGCAGCTCCTGCGCGTTCTGGC TCGTCGTCTGCGTCGCACCAACGCTTCCCTGGCTGA CCTCATCTTCACCGACGTCCCAGGCCGCGTTGCTAA GACCCTTCTGCAGCTGGCTAACCGCTTCGGCACCC AAGAAGCTGGCGCGCTGCGCGTGAACCACGACCTC ACTCAGGAAGAAATCGCACAGCTCGTCGGTGCTTCC CGTGAAACTGTGAATAAGGCTCTTGCAACGTTCGCA CACCGTGGCTGGATTCGCCTCGAGGGCAAGTCCGT CCTCATTGTGGACACCGAGCATTTGGCACGTCGCG CTCGATAA | SEQ ID NO: 2 |

Herein, the term, “corresponding to” refers to an amino acid residue at a position listed in a polypeptide, or an amino acid residue that is similar, identical or homologous to a residue listed in a polypeptide. Confirming the amino acid at the corresponding position may be determining a specific amino acid in a sequence that refers to a specific sequence. “Corresponding region” used herein generally refers to a similar or corresponding position in a related protein or reference protein.

For example, any amino acid sequence is aligned with SEQ ID NO: 1, and based on this, each amino acid residue of the amino acid sequence may be numbered by reference to the numerical position of the amino acid residue of SEQ ID NO: 1 and the corresponding amino acid residue. For example, a sequence alignment algorithm such as that described herein may confirm the position of an amino acid, or a position where a modification such as substitution, insertion or deletion occurs compared to a query sequence (also referred to as a “reference sequence”).

For such alignment, for example, Needleman-Wunsch algorithm (Needleman and Wunsch, 1970, J. Mol. Biol. 48: 443-453), Needle program of EMBOSS package (EMBOSS: The European Molecular Biology Open Software Suite, Rice et al., 2000), Trends Genet. 16: 276-277), and the like may be used, but not limited thereto, and sequence alignment programs, pairwise sequence comparison algorithm, and the like known in the art may be appropriately used.

Herein, that a polynucleotide or polypeptide “comprises a specific nucleic acid sequence (nucleotide sequence) or amino acid sequence or consists of the sequence” may mean that the polynucleotide or polypeptide necessarily comprises the specific nucleic acid sequence (nucleotide sequence) or amino acid sequence, and it may be interpreted as including the “substantially equivalent sequence” in which mutation (deletion, substitution, modification and/or insertion) is added to the specific nucleic acid sequence (nucleotide sequence) or amino acid sequence (or not excluding such mutation) within the range of maintaining the original function and/or desired function of the polynucleotide or polypeptide. In one example, that a polynucleotide or polypeptide “comprises a specific nucleic acid sequence (nucleotide sequence) or amino acid sequence or consists of the sequence” may mean that the polynucleotide or polypeptide (i) necessarily comprises the specific nucleic acid sequence (nucleotide sequence) or amino acid sequence, or (ii) consists of the nucleic acid sequence or amino acid sequence having homology or identity of 70% or more, 80% or more, 85% or more, 90% or more, 91% or more, 92% or more, 93% or more, 94% or more, 95% or more, 96% or more, 97% or more, 98% or more, 98% or more, 99% or more, 99.5% or more, or 99.9% or more to the specific nucleic acid sequence (nucleotide sequence) or amino acid sequence or necessarily comprises that and maintains the original function and/or desired function. In one example, the desired function may mean a function of increasing or giving the L-threonine productivity of a microorganism.

Herein, “homology” means the percent of identity between two polynucleotide or polypeptide moieties. The homology between sequences from one moiety to the other moiety may be determined by known art. For example, homology may be determined by directly aligning sequence information between two polynucleotide molecules or two polypeptide molecules using a readily available computer program aligning sequence information, for example, parameters such as score, identity and similarity, and the like. The computer program may be BLAST (NCBI), CLC Main Workbench (CLC bio), MegAlign™ (DNASTAR Inc), and the like. In addition, the homology between polynucleotides may be determined by hybridizing polynucleotides under conditions of forming a stable double strand between homologous regions, and then degrading them with single-stranded-specific nuclease to confirm the size of the degraded fragment.

Herein, ‘homology or identity’ means the degree of similarity between two given amino acid sequences or nucleotide sequences and may be expressed as a percentage. The terms, homology and identity may be often used interchangeably.

The sequence homology or identity of the conserved polynucleotide or polypeptide is determined by a standard arrangement algorithm, and a default gap penalty established by a used program may be used together. Substantially, homologous or identical sequence may be generally hybridized under moderate or high stringent conditions with all or part of a sequence. It is obvious that hybridization also includes hybridization with a polynucleotide containing a codon in consideration of a general codon or codon degeneracy in a polynucleotide.

Whether any two polynucleotide or polypeptide sequences have homology, similarity or identity may be determined, for example, using a known computer algorithm such as "FASTA" program using a default parameter such as Pearson et al (1988) [Proc. Natl. Acad. Sci. USA 85]: 2444. Otherwise, it may be determined using Needleman-Wunsch algorithm (Needleman and Wunsch, 1970, J. Mol. Biol. 48: 443-453), as performed in the Needleman program of EMBOSS package (EMBOSS: The European Molecular Biology Open Software Suite, Rice et al., 2000, Trends Genet. 16: 276-277) (version 5.0.0 or later version) (including GCG program package (Devereux, J., et al, Nucleic Acids Research 12: 387 (1984)), BLASTP, BLASTN, FASTA (Atschul, [S.][F.,][ET AL, J MOLEC BIOL 215]: 403 (1990); Guide to Huge Computers, Martin J. Bishop, [ED.,] Academic Press, San Diego, 1994, and [CARILLO ETA/.](1988) SIAM J Applied Math 48: 1073). For example, the homology, similarity or identity may be determined using BLAST or ClustalW of National Center for Biotechnology Information.

The homology, similarity or identity of the polynucleotide or polypeptide may be determined by comparing sequence information, for example, using GAP computer program such as Needleman et al. (1970), J Mol Biol. 48:443, for example, known in Smith and Waterman, Adv. Appl. Math (1981) 2:482. In summary, the GAP program may be defined as a value of dividing the number of similarly aligned symbols (i.e., nucleotide or amino acid) by the total number of symbols in the shorter of two sequences. The default parameter for the GAP program may comprise (1) binary comparison matrix (containing values of 1 for identity and 0 for non-identity) and weighted comparison matrix of Gribskov et al (1986) Nucl. Acids Res. 14: 6745 disclosed in Schwartz and Dayhoff, eds., Atlas Of Protein Sequence And Structure, National Biomedical Research Foundation, pp. 353-358 (1979) (or EDNAFULL (EMBOSS version of NCBI NUC4.4) substitution matrix); (2) 3.0 penalty for each gap and additional 0.10 penalty for each symbol in each gap (or gap opening penalty 10, gap extending penalty 0.5); and (3) no penalty for end gaps.

One aspect may provide a GlxR protein variant in which an amino acid at a position of one or more selected from the group consisting of the 45$^{th}$, 66$^{th}$, 166$^{th}$ and 168$^{th}$ from the N-terminus in the amino acid sequence of SEQ ID NO: 1 and/or corresponding thereto (to one or more positions selected above) is substituted with other amino acid. The "other amino acid" may mean other amino acid except for amino acids positioned at a position of one or more selected from the group consisting of the 45$^{th}$, 66$^{th}$, 166$^{th}$ and 168$^{th}$ of SEQ ID NO: 1 and/or corresponding thereto.

The variant according to one example may comprise a polypeptide in which an amino acid residue at a position of one or more selected from the group consisting of the 45$^{th}$, 66$^{th}$, 166$^{th}$ and 168$^{th}$ of the amino acid sequence of SEQ ID NO: 1 and/or corresponding thereto (at one or more positions selected above) is substituted with other kind of amino acid residue in the amino acid sequence having homology or identity of at least 70%, 75%, 80%, 85%, 90%, 95%, 96%, 97%, 98%, 99%, 99.5%, 99.7% or 99.9% or more, to the amino acid sequence represented by SEQ ID NO: 1. In addition, it is obvious that variants having an amino acid sequence in which some sequences are deleted, modified, substituted, conservatively substituted or added are also included within the scope of the present application, if the protein has such homology or identity and has the same or corresponding activity to the GlxR protein.

In one example, a GlxR (glyoxylate bypass regulator) protein variant, comprising a mutation selected from the group consisting of (1) to (4) below:

(1) substitution of the residue corresponding to the 45$^{th}$ amino acid position from the N-terminus in the amino acid sequence of SEQ ID NO: 1 (for example, glutamic acid, or glutamate) with alanine, serine, phenylalanine or lysine;

(2) substitution of the residue corresponding to the 66$^{th}$ amino acid position from the N-terminus in the amino acid sequence of SEQ ID NO: 1 (for example, aspartic acid, or aspartate) with alanine, phenylalanine or lysine;

(3) substitution of the residue corresponding to the 166$^{th}$ amino acid position from the N-terminus in the amino acid sequence of SEQ ID NO: 1 (for example, threonine) with aspartic acid, phenylalanine or lysine; and (4) substitution of the residue corresponding to the 168$^{th}$ amino acid position from the N-terminus in the amino acid sequence of SEQ ID NO: 1 (for example, glutamic acid, or glutamate) with alanine, phenylalanine or lysine.

In addition, the variant of the present application may comprise an amino acid in which an amino acid residue at a position of one or more selected from the group consisting of the 45$^{th}$, 66$^{th}$, 166$^{th}$ and 168$^{th}$ based on the amino acid sequence of SEQ ID NO: 1 and/or corresponding thereto (at one or more positions selected above) is substituted with other kind of amino acid residue, which has homology or identity of at least 70%, 75%, 80%, 85%, 90%, 95%, 96%, 97%, 98%, 99%, 99.5%, 99.7% or 99.9% or more to the amino acid sequence selected from SEQ ID NOs: 3 to 15. Furthermore, it is obvious that variants having an amino acid sequence in which some sequences are deleted, modified, substituted, conservatively substituted or added are also included within the scope of the present application, if the amino acid sequence has such homology or identity and exhibits the corresponding effect to the variant of the present application.

For example, there are cases of having a sequence insertion or deletion which does not alter the function of the variant of the present application at the N-terminus, C-terminus and/or within the amino acid sequence, naturally occurring mutation, silent mutation or conservative substitution.

The "conservative substitution" means substituting an amino acid with another amino acid having similar structural and/or chemical properties. Such amino acid substitution may generally occur based on similarity in the polarity, charge, solubility, hydrophobicity, hydrophilicity and/or amphipathic nature of the residue. Typically, the conservative substitution may have little or no effect on the activity of protein or polypeptide.

Herein, the term "variant" refers to a polypeptide in which one or more amino acids are conservatively substituted and/or modified so as to be different from the amino acid sequence before mutation of the variant, but functions or properties are maintained. Such variant may generally be identified by modifying one or more amino acids in the amino acid sequence of the polypeptide and evaluating the properties of the modified polypeptide. In other words, the ability of the variant may be increased, unchanged or decreased, compared to the polypeptide before mutation. In addition, some variants may include variants in which one or more portions such as an N-terminal leader sequence or a transmembrane domain are removed. Other variants may include variants in which a portion has been removed from the N- and/or C-terminus of the mature protein. The term "variant" may be used interchangeably with terms such as mutant, modification, mutant polypeptide, mutated protein, mutation and variant, and the like (in English, modification, modified polypeptide, modified protein, variant, mutein, divergent, etc.), and as long as it is a term used in a mutated sense, it is not limited thereto. In addition, the variant may comprise deletion or insertion of amino acids having minimal effect on the properties and secondary structure of the polypeptide. For example, a signal (or leader) sequence involved in co-translational or post-translational protein translocation may be conjugated at the N-terminus of the variant. Furthermore, the variant may be conjugated with other sequences or linkers for identification, purification or synthesis.

According to one example, the GlxR protein variant may comprise the amino acid sequence selected from the group consisting of SEQ ID NO: 3 to SEQ ID NO: 15 or consist of the amino acid sequence. The amino acid sequences of SEQ ID NO: 3 to SEQ ID NO: 15 are described in Table 2 below.

TABLE 2

| Name | Sequence | SEQ ID NO |
|---|---|---|
| GlxR_E45A | MEGVQEILSRAGIFQGVDPTAVNNLIQDMETVRFPRGA<br>TIFDEGAPGDRLYIITSGKVKLARHAPDGRENLLTIMGP<br>SDMFGELSIFDPGPRTSSAVCVTEVHAATMNSDMLRN<br>WVADHPAIAEQLLRVLARRLRRTNASLADLIFTDVPGR<br>VAKTLLQLANRFGTQEAGALRVNHDLTQEEIAQLVGAS<br>RETVNKALATFAHRGWIRLEGKSVLIVDTEHLARRAR | SEQ ID NO: 3 |
| GlxR_E45S | MEGVQEILSRAGIFQGVDPTAVNNLIQDMETVRFPRGA<br>TIFDEGSPGDRLYIITSGKVKLARHAPDGRENLLTIMGP<br>SDMFGELSIFDPGPRTSSAVCVTEVHAATMNSDMLRN<br>WVADHPAIAEQLLRVLARRLRRTNASLADLIFTDVPGR<br>VAKTLLQLANRFGTQEAGALRVNHDLTQEEIAQLVGAS<br>RETVNKALATFAHRGWIRLEGKSVLIVDTEHLARRAR | SEQ ID NO: 4 |
| GlxR_E45F | MEGVQEILSRAGIFQGVDPTAVNNLIQDMETVRFPRGA<br>TIFDEGFPGDRLYIITSGKVKLARHAPDGRENLLTIMGP<br>SDMFGELSIFDPGPRTSSAVCVTEVHAATMNSDMLRN<br>WVADHPAIAEQLLRVLARRLRRTNASLADLIFTDVPGR<br>VAKTLLQLANRFGTQEAGALRVNHDLTQEEIAQLVGAS<br>RETVNKALATFAHRGWIRLEGKSVLIVDTEHLARRAR | SEQ ID NO: 5 |
| GlxR_E45K | MEGVQEILSRAGIFQGVDPTAVNNLIQDMETVRFPRGA<br>TIFDEGKPGDRLYIITSGKVKLARHAPDGRENLLTIMGP<br>SDMFGELSIFDPGPRTSSAVCVTEVHAATMNSDMLRN<br>WVADHPAIAEQLLRVLARRLRRTNASLADLIFTDVPGR<br>VAKTLLQLANRFGTQEAGALRVNHDLTQEEIAQLVGAS<br>RETVNKALATFAHRGWIRLEGKSVLIVDTEHLARRAR | SEQ ID NO: 6 |
| GlxR_D66A | MEGVQEILSRAGIFQGVDPTAVNNLIQDMETVRFPRGA<br>TIFDEGEPGDRLYIITSGKVKLARHAPAGRENLLTIMGP<br>SDMFGELSIFDPGPRTSSAVCVTEVHAATMNSDMLRN<br>WVADHPAIAEQLLRVLARRLRRTNASLADLIFTDVPGR<br>VAKTLLQLANRFGTQEAGALRVNHDLTQEEIAQLVGAS<br>RETVNKALATFAHRGWIRLEGKSVLIVDTEHLARRAR | SEQ ID NO: 7 |
| GlxR_D66F | MEGVQEILSRAGIFQGVDPTAVNNLIQDMETVRFPRGA<br>TIFDEGEPGDRLYIITSGKVKLARHAPFGRENLLTIMGP<br>SDMFGELSIFDPGPRTSSAVCVTEVHAATMNSDMLRN<br>WVADHPAIAEQLLRVLARRLRRTNASLADLIFTDVPGR<br>VAKTLLQLANRFGTQEAGALRVNHDLTQEEIAQLVGAS<br>RETVNKALATFAHRGWIRLEGKSVLIVDTEHLARRAR | SEQ ID NO: 8 |
| GlxR_D66K | MEGVQEILSRAGIFQGVDPTAVNNLIQDMETVRFPRGA<br>TIFDEGEPGDRLYIITSGKVKLARHAPKGRENLLTIMGP<br>SDMFGELSIFDPGPRTSSAVCVTEVHAATMNSDMLRN<br>WVADHPAIAEQLLRVLARRLRRTNASLADLIFTDVPGR<br>VAKTLLQLANRFGTQEAGALRVNHDLTQEEIAQLVGAS<br>RETVNKALATFAHRGWIRLEGKSVLIVDTEHLARRAR | SEQ ID NO: 9 |
| GlxR_T166D | MEGVQEILSRAGIFQGVDPTAVNNLIQDMETVRFPRGA<br>TIFDEGEPGDRLYIITSGKVKLARHAPDGRENLLTIMGP<br>SDMFGELSIFDPGPRTSSAVCVTEVHAATMNSDMLRN<br>WVADHPAIAEQLLRVLARRLRRTNASLADLIFTDVPGR<br>VAKTLLQLANRFGDQEAGALRVNHDLTQEEIAQLVGAS<br>RETVNKALATFAHRGWIRLEGKSVLIVDTEHLARRAR | SEQ ID NO: 10 |
| GlxR_T166F | MEGVQEILSRAGIFQGVDPTAVNNLIQDMETVRFPRGA<br>TIFDEGEPGDRLYIITSGKVKLARHAPDGRENLLTIMGP<br>SDMFGELSIFDPGPRTSSAVCVTEVHAATMNSDMLRN<br>WVADHPAIAEQLLRVLARRLRRTNASLADLIFTDVPGR<br>VAKTLLQLANRFGFQEAGALRVNHDLTQEEIAQLVGAS<br>RETVNKALATFAHRGWIRLEGKSVLIVDTEHLARRAR | SEQ ID NO: 11 |

TABLE 2-continued

| Name | Sequence | SEQ ID NO |
|---|---|---|
| GlxR_T166K | MEGVQEILSRAGIFQGVDPTAVNNLIQDMETVRFPRGA TIFDEGEPGDRLYIITSGKVKLARHAPDGRENLLTIMGP SDMFGELSIFDPGPRTSSAVCVTEVHAATMNSDMLRN WVADHPAIAEQLLRVLARRLRRTNASLADLIFTDVPGR VAKTLLQLANRFGKQEAGALRVNHDLTQEEIAQLVGAS RETVNKALATFAHRGWIRLEGKSVLIVDTEHLARRAR | SEQ ID NO: 12 |
| GlxR_E168A | MEGVQEILSRAGIFQGVDPTAVNNLIQDMETVRFPRGA TIFDEGEPGDRLYIITSGKVKLARHAPDGRENLLTIMGP SDMFGELSIFDPGPRTSSAVCVTEVHAATMNSDMLRN WVADHPAIAEQLLRVLARRLRRTNASLADLIFTDVPGR VAKTLLQLANRFGTQAAGALRVNHDLTQEEIAQLVGAS RETVNKALATFAHRGWIRLEGKSVLIVDTEHLARRAR | SEQ ID NO: 13 |
| GlxR_E168F | MEGVQEILSRAGIFQGVDPTAVNNLIQDMETVRFPRGA TIFDEGEPGDRLYIITSGKVKLARHAPDGRENLLTIMGP SDMFGELSIFDPGPRTSSAVCVTEVHAATMNSDMLRN WVADHPAIAEQLLRVLARRLRRTNASLADLIFTDVPGR VAKTLLQLANRFGTQFAGALRVNHDLTQEEIAQLVGAS RETVNKALATFAHRGWIRLEGKSVLIVDTEHLARRAR | SEQ ID NO: 14 |
| GlxR_E168K | MEGVQEILSRAGIFQGVDPTAVNNLIQDMETVRFPRGA TIFDEGEPGDRLYIITSGKVKLARHAPDGRENLLTIMGP SDMFGELSIFDPGPRTSSAVCVTEVHAATMNSDMLRN WVADHPAIAEQLLRVLARRLRRTNASLADLIFTDVPGR VAKTLLQLANRFGTQKAGALRVNHDLTQEEIAQLVGAS RETVNKALATFAHRGWIRLEGKSVLIVDTEHLARRAR | SEQ ID NO: 15 |

The GlxR protein variant according to one example is a global transcriptional regulator, as GlxR protein before mutation (for example, GlxR protein consisting of the amino acid sequence of SEQ ID NO: 1), and for example, it may have the function of the regulator for glyoxylate bypass genes (for example, ace A and/or ace B).

The GlxR protein variant according to one example may have a weakened activity than the GlxR protein (a wildtype protein (for example, GlxR protein consisting of the amino acid sequence of SEQ ID NO: 1)) before mutation. The "weakened activity of the GlxR protein" may mean that the level of activity of the global transcriptional regulator in the cell is reduced compared to the protein before mutation. The weakening is when the activity of the protein itself is reduced compared to the activity of the protein possessed by the original microorganism (for example, wildtype, parent strain, host microorganism, unmodified microorganism, etc.) due to mutation of the gene encoding GlxR protein, and when the expression level of the enzyme is lowered due to inhibition of transcription and/or inhibition of translation of the gene encoding GlxR protein, and thus the overall degree of enzymatic activity in the cell is low, a combination thereof may also be included.

Herein, the GlxR protein variant may be used as the same meaning as mutant GlxR protein, GlxR variant and mutant GlxR.

Another aspect may provide a polynucleotide, encoding the GlxR protein variant.

Herein, "polynucleotide" refers to a DNA or RNA strand of a certain length or longer as a polymer of nucleotides in which nucleotide monomers are connected in a long chain form by covalent bonds, and more specifically, a polynucleotide fragment encoding the variant.

The polynucleotide may be included without limitation, as long as it is a polynucleotide sequence encoding the GlxR protein variant according to one example. The polynucleotide according to one example may comprise a nucleic acid sequence encoding a GlxR protein variant in which an amino acid at a position of one or more selected from the group consisting of the $45^{th}$, $66^{th}$, $166^{th}$ and $168^{th}$, from the N-terminus in the amino acid sequence of SEQ ID NO: 1 and/or corresponding thereto (at one or more positions selected above), or consist of the nucleic acid sequence, and for example, it may comprise a nucleic acid sequence encoding the amino acid sequence selected from the group consisting of SEQ ID NO: 3 to SEQ ID NO: 15 or consist of the nucleic acid sequence.

The polynucleotide may have various modifications in the coding region within a range which does not change the amino acid sequence of the variant according to one example, considering codon degeneracy or preferred codons in organisms that want to express the variant according to one example. Accordingly, by codon degeneracy, the polypeptide consisting of the amino acid sequence of SEQ ID NO: 3 to SEQ ID NO: 15 or a polynucleotide capable of encoding a polypeptide having homology (or identity) thereto may also be included.

The polynucleotide according to one example may be included without limitation, as long as it is a probe that may be prepared from a known gene sequence, for example, a sequence capable of hybridizing under a stringent condition with a complementary sequence to all or part o the polynucleotide according to one example. The "stringent condition" means a condition that enables specific hybridization between polynucleotides.

This condition is specifically described in the document (See J. Sambrook et al., Molecular Cloning, A Laboratory Manual, 2nd Edition, Cold Spring Harbor Laboratory press, Cold Spring Harbor, New York, 1989; F. M. Ausubel et al., Current Protocols in Molecular Biology, John Wiley & Sons, Inc., New York, 9.50-9.51, 11.7-11.8). For example, a condition in which polynucleotides with high homology or identity, polynucleotides with homology or identity of 70% or more, 75% or more, 80% or more, 85% or more, 90% or more, 95% or more, 96% or more, 97% or more, 98% or more, or 99% or more, are hybridized, and polynucleotides with low homology or identity are not hybridized, or a condition for washing once, specifically, twice or 3 times, at a salt concentration and temperature corresponding to a common southern hybridization washing condition of 60° C., 1×SSC, 0.1% SDS, specifically, 60° C., 0.1×SSC, 0.1% SDS, more specifically, 68° C., 0.1×SSC, 0.1% SDS.

Hybridization requires that two nucleic acids have complementary sequences, although mismatch between bases is possible depending on the stringency of hybridization. Herein, "complementary" is used to describe the relationship between nucleotide bases capable of hybridizing to each other. For example, with respect to DNA, adenine is complementary to thymine and cytosine is complementary to guanine. Thus, the polynucleotide according to one example may also comprise an isolated nucleic acid fragment complementary to the overall sequence as well as substantially similar nucleic acid sequences.

Specifically, the polynucleotide having homology or identity to the polynucleotide according to one example may be detected using a hybridization condition including hybridizing at a Tm value of 50° C. to 65° C. (for example, 55° C.) using the aforementioned condition. In addition, the Tm value may be 60° C., 63° C. or 65° C., but not limited thereto, and it may be appropriately adjusted by those skilled in the art according to the purpose.

The appropriate stringency for hybridizing the polynucleotide depends on the length and degree of complementarity of the polynucleotide, and the parameters are well known in the art (for example, see J. J. Sambrook et al., Molecular Cloning, A Laboratory Manual, 2nd Edition, Cold Spring Harbor Laboratory press, Cold Spring Harbor, New York, 1989; F. M. Ausubel et al., Current Protocols in Molecular Biology, John Wiley & Sons, Inc., New York, 9.50-9.51, 11.7-11.8).

Other aspect may provide a vector, comprising the polynucleotide. The vector may be an expression vector for expressing the polynucleotide in a host cell, but not limited thereto.

Herein, "vector" may comprise a DNA product comprising a nucleotide sequence of a polynucleotide encoding the target polypeptide operably linked to a suitable expression control region (or expression control sequence) so as to express a target polypeptide in a suitable host. the expression control region may comprise a promoter capable of initiating transcription, any operator sequence for regulating such transcription, a sequence encoding a suitable mRNA ribosome binding site, and a sequence regulating termination of transcription and translation. The vector may be replicated or function independently of the host genome and may be integrated into the genome itself, after being transformed into an appropriate host cell.

The vector used herein is not particularly limited, and any vector known in the art may be used. The example of the commonly used vector may include a natural or recombinant plasmid, a cosmid, a virus and a bacteriophage. For example, as a phage vector or cosmid vector, pWE15, M13, MBL3, MBL4, IXII, ASHII, APII, t10, t11, Charon4A, and Charon21A, and the like may be used, and as a plasmid vector, pDZ-based, pBR-based, pUC-based, pBluescriptII-based, pGEM-based, pTZ-based, pCL-based and pET-based, and the like may be used. Specifically, pDZ, pDC, pDCM2, pACYC177, pACYC184, pCL, pECCG117, pUC19, pBR322, pMW118, pCC1BAC vectors, and the like may be used.

In one example, a polynucleotide encoding a protein (for example, GlxR protein) in chromosome may be replaced with a mutated polynucleotide through a vector for intracellular chromosome insertion. the insertion into the chromosome of the polynucleotide may be achieved by any method known in the art, for example, homologous recombination, but not limited thereto. A selection marker for confirming the chromosome insertion may be further comprised. The selection marker is used to select cells transformed with the vector, that is, to confirm whether a target polynucleotide molecule is inserted, and markers conferring selectable phenotypes such as drug resistance, auxotrophy, resistance to cytotoxic agents or expression of surface mutant protein may be used. In an environment treated with a selective agent, only the cells expressing the selectable marker survive or exhibit other expression traits, so that the transformed cells may be selected.

Herein, "transformation" means introducing a vector comprising a polynucleotide encoding a target polynucleotide into a host cell or microorganism so that the polypeptide encoded by the polynucleotide may be expressed in the host cell. the transformed polynucleotide may include all of them regardless of whether they are inserted into the chromosome of the host cell or located outside the chromosome, as long as they can be expressed in the host cell. In addition, the polynucleotide comprises DNA and/or RNA encoding a target polypeptide (for example, the GlxR variant). The polynucleotide may be introduced in any form as long as it may be introduced and expressed into a host cell. For example, the polynucleotide may be introduced into a host cell in the form of an expression cassette, which is a gene construct including all elements necessary for self-expression. the expression cassette may comprise a promoter, a transcription termination signal, a ribosome binding site and a translation termination signal, which are usually operably linked to the polynucleotide. The expression cassette may be in the form of an expression vector capable of self-replication. In addition, the polynucleotide may be introduced into a host cell in its own form and operably linked to a sequence required for expression in the host cell, but is not limited thereto. The transformation method is included without limitation as long as it is a method of introducing a gene into a cell, and may be performed by selecting a suitable standard technique known in the art depending on the host cell. For example, electroporation, calcium phosphate ($CaPO_4$) precipitation, calcium chloride ($CaCl_2$)) precipitation, microinjection, retroviral infection, polyethylene glycol (PEG) method, DEAE-dextran method, cation liposome method, and/or lithium acetate-DMSO method, and the like may be used, but not limited thereto.

The vector may be a DNA product containing a nucleic acid sequence of a polynucleotide encoding the target protein operably linked to a suitable regulatory sequence to allow expression of the target protein (for example, the GlxR variant) in a suitable host. The regulatory sequence may include a promoter capable of initiating transcription, any operator sequence for regulating such transcription, a sequence encoding a suitable mRNA ribosome binding site and a sequence regulating termination of transcription and translation. The vector may be replicated or function independently of the host genome and may be integrated into the genome itself, after being transformed into an appropriate host cell.

Herein, "operably linked" means that the polynucleotide sequence is functionally linked to a promoter sequence that initiates and mediates transcription of the polynucleotide encoding the target variant of the present application.

Other aspect may provide a microorganism (or, strain, recombinant cell), comprising one or more kinds selected from the group consisting of the GlxR protein variant, a polynucleotide encoding the GlxR protein variant, and a vector comprising the polynucleotide. Herein, "microorganism" may include one-celled bacteria.

Herein, "strain (or, microorganism)" includes both wild-type microorganisms and microorganisms that have undergone natural or artificial genetic modification, and is a microorganism in which a specific mechanism is weakened or enhanced due to causes such as insertion of an external gene or intensification or inactivation of the activity of an endogenous gene, which is a microorganism comprising a genetic modification for production of a desired polypeptide, protein or product.

The microorganism (or, strain, recombinant cell) may be a strain comprising one or more selected from the GlxR protein variant, polynucleotide according to one example and vector comprising the polynucleotide according to one example; a strain modified to express the GlxR protein variant or polynucleotide according to one example; a strain (for example, recombinant strain) expressing the GlxR protein variant or polynucleotide according to one example; or a strain (for example, recombinant strain) having the GlxR protein variant activity, but not limited thereto.

In one example, the microorganism (or, strain, recombinant cell) may have the threonine (for example, L-threonine) productivity. The microorganism (or, strain, recombinant cell) may have the enhanced threonine productivity than a non-modified microorganism, a cell before recombination, a parent strain and/or a wildtype strain, or may be given the threonine productivity different from the non-modified microorganism, a cell before recombination, a parent strain and/or a wildtype strain, which have no threonine productivity.

Herein, "have threonine (for example, L-threonine) productivity" means a cell and/or microorganism naturally having the threonine productivity, or a microorganism in which the threonine productivity is given to a parent strain having no threonine productivity. It may be used to mean the case that the microorganism has the L-threonine productivity by introducing the GlxR protein variant according to one example and/or the case that the microorganism has the L-threonine productivity by introducing the GlxR protein variant into a microorganism having no L-threonine productivity. For example, a *Corynebacterium* sp. microorganism having the L-threonine productivity may mean a native microorganism itself or a *Corynebacterium* sp. microorganism having the enhanced L-threonine productivity in which an external gene related to threonine production mechanism is inserted or the activity of an intrinsic gene is strengthened, or weakened or inactivated.

The microorganism in which the GlxR protein mutation according to one example is introduced may have increased threonine (for example, L-threonine), compared to the same kind of non-modified microorganism. Herein, "non-modified microorganism" does not exclude strains comprising a mutation which can occur naturally in microorganisms, and may mean a wildtype strain or natural-type strain itself, or a strain before the trait is changed due to genetic mutation caused by natural or artificial factors. For example, the non-modified microorganism may mean a strain in which the GlxR variant according to one example is not introduced or before introduction. The "non-modified microorganism" may be interchangeably used with "strain before modification", "microorganism before modification", "non-mutated strain", "non-modified strain", "non-mutated microorganism" or "standard microorganism". That the GlxR protein mutation is introduced into a microorganism above may mean that the GlxR protein variant, a polynucleotide encoding the GlxR protein variant and/or a vector comprising the polynucleotide. In one example, the protein non-modified microorganism, which is a subject strain comparing the increase of the threonine productivity may be ATCC13032 strain, KCCM12000P strain, and/or KCCM12120P strain, but not limited thereto.

In one example, the recombinant strain with increased productivity may have increased threonine productivity of about 1% or more, about 2.5% or more, about 5% or more, about 6% or more, about 7% or more, about 8% or more, about 9% or more, about 10% or more, about 10.5% or more, about 11% or more, about 11.5% or more, about 12% or more, about 12.5% or more, about 13% or more, about 13.5% or more, about 14% or more, about 14.5% or more, about 15% or more, about 15.5% or more, about 16% or more, about 16.5% or more, about 17% or more, about 17.5% or more, about 18% or more, about 18.5% or more, about 19% or more, about 19.5% or more, about 20% or more, about 20.5% or more, about 21% or more, about 21.5% or more, about 22% or more, about 22.5% or more, about 23% or more, about 23.5% or more, about 24% or more, about 24.5% or more, about 25% or more, about 25.5% or more, about 26% or more, about 26.5% or more, about 27% or more, (the upper limit is not particularly limited, and for example, about 200% or less, about 150% or less, about 100% or less, about 50% or less, about 45% or less, about 40% or less, or about 35% or less), compared to the parent strain before mutation or non-modified microorganism. In other example, the recombinant strain with increased productivity may have increased threonine productivity of about 1.1 times or more, about 1.12 times or more, about 1.13 times or more, 1.15 times or more, 1.16 times or more, 1.17 times or more, 1.18 times or more, 1.19 times or more, about 1.2 times or more, about 1.25 times or more, about 1.26 times or more, or about 1.3 times or more (the upper limit is not particularly limited, and for example, about 10 times or less, about 5 times or less, about 3 times or less, or about 2 times or less), compared to the parent strain before mutation or non-modified microorganism. In other example, the recombinant strain with increased productivity may have increased threonine productivity of about 1.1 times or more, about 1.12 times or more, compared to the parent strain before mutation or non-modified microorganism. The term, "about" is a range including all of ±0.5, ±0.4, ±0.3, ±0.2, ±0.1, and the like, and it includes all numerical values within a range equal or similar to the numerical value following the term about.

The insertion of the polynucleotide into host cell genome (chromosome) or introduction of mutation so that a host cell endogenous gene (for example, glxR gene) encodes a GlxR protein variant may be performed by appropriately selecting a known method by those skilled in the art, and for example, it may be performed using an RNA-guided endonuclease system; for example, (a) RNA-guided endonuclease (e.g., Cas9 protein, etc.), its encoding gene, or a vector comprising the gene; and (b) guided RNA (e.g., single guide RNA (sgRNA), etc.), its encoding DNA, or a mixture comprising a vector comprising the DNA (for example, a mixture of the RNA-guided endonuclease protein and guided RNA, etc.), or a complex (for example, one or more selected from the group consisting of ribonucleic acid fusion protein (RNP), a recombinant vector (for example, a vector comprising the RNA-guided endonuclease encoding gene and guided RNA encoding DNA together, etc.), and the like), but not limited thereto. Modification of a part or all of a polynucleotide in the microorganism according to one example (for example, modification for encoding the aforementioned protein variant) may be induced by (a) homologous recombination using a vector for insertion of chromosome into a microorganism or genome editing using a gene scissor (engineered nuclease, e.g., CRISPR-Cas9) and/or (b) light and/or chemical substance treatment such as ultraviolet and radiation, and the like, but not limited thereto. The method for modifying part or all of the gene may include a method by DNA recombination technology. For example, a part or all of the gene may be deleted by injecting a nucleotide sequence or vector comprising a nucleotide sequence having homology to a target gene to cause homologous recombination. The nucleotide sequence or vector to be injected may comprise a dominant selectable marker, but not limited thereto.

The microorganism (or strain, recombinant cell) may further comprise mutation to increase threonine production, and the position of the mutation and/or kind of the gene and/or protein to be mutated may be comprised without limitation as long as it increases threonine production. The recombinant cell may be used without limitation as long as it is a transformable cell.

In order to distinguish from a microorganism in which the threonine productivity is increased or the threonine productivity is given by introducing the GlxR protein mutation, the microorganism before introducing the GlxR protein mutation may be represented by a host microorganism (or parent strain, non-modified microorganism).

In one example, the microorganism comprising the GlxR protein variant, a polynucleotide encoding the variant, and/or a vector comprising the polynucleotide may, (i) further comprise the polynucleotide and/or the recombinant vector, in addition to genome, and/or (ii) comprise the polynucleotide, as an endogenous GlxR protein encoding gene (for example, gIxR gene).

The (ii) "comprising the polynucleotide, as an endogenous GlxR protein encoding gene (for example, gIxR gene)" may mean (a) that the polynucleotide is comprised (inserted) by replacing the endogenous GlxR protein encoding gene (for example, gIxR gene), and/or (b) that the endogenous GlxR protein encoding gene (for example, gIxR gene) is mutated to have the nucleic acid sequence of the polynucleotide (that is, nucleic acid sequence encoding GlxR protein variant) by gene editing technology.

In one example, the GlxR protein or a gene encoding the same may be derived from a host microorganism (intrinsic) or derived from a different microorganism (foreign).

In one example, in the microorganism (or strain, recombinant cell), the polynucleotide according to one example may be integrated in the chromosome, and for example, the polynucleotide according to one example may be replaced for the native gene at the gIxR gene site in the chromosome or be integrated at the additional gene site.

The microorganism may be a *Corynebacterium* sp. microorganism.

The *Corynebacterium* sp. microorganism may include *Corynebacterium glutamicum, Corynebacterium ammoniagenes, Corynebacterium acetoacidophilum, Corynebacterium acetoglutamicum, Corynebacterium alkanolyticum, Corynebacterium callunae, Corynebacterium lilium, Corynebacterium melassecola, Corynebacterium thermoaminogenes, Corynebacterium efficiens, Corynebacterium herculis, Corynebacterium crudilactis, Corynebacterium deserti, Corynebacterium stationis, Corynebacterium singulare, Corynebacterium halotolerans, Corynebacterium striatum, Corynebacterium ammoniagenes, Corynebacterium pollutisoli, Corynebacterium imitans, Corynebacterium testudinoris*, and/or *Corynebacterium flavescens*, and the like.

The microorganism (or strain, recombinant cell) may include both one artificially prepared by transformation, or naturally occurring one. For example, the microorganism (or strain, recombinant cell) may be transformed with a vector comprising a polynucleotide encoding the GlxR protein variant according to one example.

The microorganism (or strain, recombinant cell) may be one in which the polynucleotide sequence according to one embodiment is integrated in the chromosome. Homologous recombination allows, in conjunction with the use of the vector according to one example, the exchange of DNA fragments on the chromosome for the polynucleotide according to one example to be delivered into a cell by the vector. For efficient recombination between circular DNA molecules of the vector and target DNA on the chromosome, in the DNA region to be exchanged containing the polynucleotide according to one example, the nucleotide sequence homologous to the target site at the end is provided, and they determine the site of integration of the vector and exchange of DNA. For example, the polynucleotide according to one example may be exchanged for a native gIxR gene at a natural gene site in the chromosome or may be integrated at an additional gene site.

Other aspect may provide a method for production of threonine, comprising culturing the microorganism (or strain, recombinant cell) in a medium. The threonine may be L-threonine. The microorganism (or strain, recombinant cell) is as described above.

Herein, "culture" refers to growing the microorganism (or strain, recombinant cell) in an appropriately controlled environmental condition. The culture may be made according to an appropriate medium and culture conditions known in the art, and it should satisfy requirements of a specific strain in an appropriate manner, and may be appropriately modified by those skilled in the art. The culture method may include for example, batch culture, continuous culture, fed-batch culture, or a combination thereof, but not limited thereto.

Herein, "medium" means a substance in which nutrients required for culturing the *Corynebacterium glutamicum* strain of the present application as a main component, and supplies nutrients and growth factors, and the like, including water which is essential for survival and growth. Specifically, the medium and other culture conditions used for culture of the microorganism according to one example may be used without particular limitation as long as it is a medium used for common culture of a microorganism, but the microorganism according to one example may be cultured while adjusting the temperature, pH, and the like under an aerobic condition in a conventional medium containing a suitable carbon source, a nitrogen source, a phosphorus source, an inorganic compound, an amino acid and/or vitamin, and the like.

In one example, the medium for culturing the microorganism (or strain, recombinant cell) may refer to the document ["Manual of Methods for General Bacteriology" by the American Society for Bacteriology (Washington D.C., USA, 1981)], but not limited thereto.

As the carbon source, carbohydrates such as glucose, saccharose, lactose, fructose, sucrose and maltose; sugar alcohols such as mannitol and sorbitol; organic acids such as pyruvate, lactate and citrate; and amino acids such as glutamic acid, methionine and lysine, and the like may be included. In addition, natural organic nutrients such as starch hydrolysate, molasses, blackstrap molasses, rice bran, cassava, sugar cane residues and corn steep liquid may be used, and specifically, carbohydrates such as glucose and sterilized pretreated molasses (that is, molasses converted to reduced sugar), and the like may be used, and other suitable amount of carbon sources may be variously used without limitation. These carbon sources may be used alone or 2 kinds or more may be used in combination, but not limited thereto.

As the nitrogen source, inorganic nitrogen sources such as ammonia, ammonium sulfate, ammonium citrate, ammonium phosphate, ammonium carbonate, ammonium nitrate, and the like; and organic nitrogen sources including amino acids such as glutamic acid, methionine, glutamine, peptone, NZ-amine, meat extract, yeast extract, malt extract, corn steep liquid, casein hydrolysate, fish or its decomposition product, defatted soybean cake or its decomposition product may be used. These nitrogen sources may be used alone or two kinds or more may be used in combination, but not limited thereto.

As the phosphorus source, potassium phosphate monobasic, potassium phosphate dibasic, or sodium-containing salts corresponding thereto, or the like may be included. As the inorganic compound, sodium chloride, calcium chloride, iron chloride, magnesium sulfate, iron sulfate, manganese sulfate, calcium carbonate, and the like may be used, and in addition, amino acids, vitamins and/or appropriate precursors, and the like may be included. These components or precursors may be added to the medium in a batch or continuous manner. However, it is not limited thereto.

Furthermore, the medium may contain a metal salt such as magnesium sulfate or iron sulfate needed for growth, but not limited thereto. In addition, essential growth materials such as amino acids and vitamins may be comprised. Moreover, precursors suitable for the medium may be used. The medium or individual component may be added in a batch or continuous manner by an appropriate method in a culture solution during the culture process, but not limited thereto.

According to one example, a compound such as ammonium hydroxide, potassium hydroxide, ammonia, phosphate, sulfate, and the like may be added to the medium during the culture in an appropriate manner, to adjust the pH of the medium. In addition, during culturing, an antifoaming agent such as fatty acid polyglycol ester may be used to inhibit bubble formation. Furthermore, in order to maintain the aerobic state of the medium, oxygen or oxygen-containing gas may be injected into the medium, or in order to maintain the anaerobic and microaerobic state, gas is not injected or nitrogen, hydrogen or carbon dioxide gas may be injected, but not limited thereto.

According to one example, the culture temperature may be maintained as 20° C. to 45° C., 25° C. to 40° C., or 30° C. to 37° C. The culture period may be continued until a useful substance (for example, L-threonine) is obtained in a desired amount, and for example, it may be 10 to 160 hours.

The production method of threonine according to one example may further comprise preparing the microorganism (or strain, recombinant cell) according to one example, preparing a medium for culturing the microorganism, or a combination thereof (in any order), for example, before the culturing.

The production method of threonine according to one example may further comprise isolating and/or recovering threonine form the cultured medium (culture medium) and/or microorganism (or strain, recombinant cell). The isolating and/or recovering may be further comprised after the culturing. The culture medium may refer to a medium culturing the microorganism (or strain, recombinant cell).

The isolating and/or recovering threonine may collect a desired amino acid (for example, L-threonine) from a medium, culture solution or microorganism using an appropriate method known in the art depending on the culture method (for example, batch, continuous or fed-batch culture method, etc.). For example, a method such as centrifugation, filtration, treatment by a crystallized protein precipitating agent (salting out method), extraction, spraying, drying, evaporation, precipitation, crystallization, ultrasonic disintegration, ultrafiltration, dialysis, electrophoresis, fractional dissolution (for example, ammonium sulfate precipitation), HPLC, and/or chromatography (for example, ion exchange, affinity, hydrophobicity, liquid and size exclusion), and the like may be used, but not limited thereto.

The production method of threonine according to one example may further comprise purifying. The purifying may be performed using an appropriate method known in the art. In one example, when the production method of threonine comprises both isolating and/or recovering and purifying, purifying threonine may be additionally comprised before or after the isolating and/or recovering, or the isolating and/or recovering and purifying may be performed at different times (or continuously) in any order, or may be performed simultaneously or by being integrated into one step, but not limited thereto.

Other aspect may provide a composition for producing threonine (for example, L-threonine), comprising one or more kinds selected from the group consisting of the GlxR protein variant, a polynucleotide encoding the GlxR protein variant, a vector comprising the polynucleotide and a microorganism (or strain, recombinant cell) comprising the polynucleotide or vector. The variant, polynucleotide, vector, microorganism, medium and threonine, and the like are as described above.

In one example, the composition for production may further comprise any appropriate excipient commonly used for a composition for producing an amino acid, and such excipient may be for example, a preservative, wetting agent, dispersant, suspending agent, buffer, stabilizer or tonicifying agent, or the like, but not limited thereto.

Other aspect may provide a method of increasing threonine (for example, L-threonine) productivity of the microorganism or a method of giving threonine (for example, L-threonine) productivity to the microorganism, comprising introducing (for example, transforming) the GlxR protein variant, a polynucleotide encoding the same and/or a recombinant vector comprising the polynucleotide into a microorganism.

Advantageous Effects

The GlxR protein variant according to one example is introduced into a microorganism, and thereby, it may reduce the production of by-products and significantly increase the productivity of threonine.

MODE FOR INVENTION

Hereinafter, the present application will be described in more detail by examples and experimental examples. However, these examples and experimental examples are intended to illustrate the present application exemplarily, but the scope of the present application is not limited by these examples and experimental examples.

Example 1: Construction of Vector Library for Introducing Mutation in gIxR Gene ORF In order to discover a variant in which the expression of GlxR protein of *Corynebacterium glutamicum* (SEQ ID NO:

1) or its activity was changed, a vector library was constructed by the following method.

At first, primers of SEQ ID NO: 16 and SEQ ID NO: 17, in which a restriction enzyme SmaI recognition site was inserted into the 5' fragment and 3' fragment at the position about 1000 bp away, back and forth, respectively, from the position of 133 to 135$^{th}$ 196 to 198$^{th}$ 496 to 498$^{th}$, and 502 to 504$^{th}$ in the nucleotide sequence (SEQ ID NO: 2) of the gIxR gene using the genomic DNA extracted from the WT strain (ATCC13032) as a template.

Specifically, DNA fragments positioned at the 5' and 3' terminuses of the gIxR gene (1000 bp each) were constructed in a form connected to the pDZ vector (Korean Patent Publication No. 10-2008-0025355). The 5' terminal gene fragment using primers of SEQ ID NOs: 16 and 18 and the 3' terminal gene fragment using primers of SEQ ID NOs: 17 and 19 were constructed through PCR using chromosome of the WT strain as a template. PCR conditions were repeating denaturation at 94° C. for 5 minutes, denaturation at 94° C. for 30 seconds, annealing at 55° C. for 30 seconds, and polymerization at 72° C. for 1 minute, 24 times, and then performing polymerization at 72° C. for 10 minutes. After purifying the amplified DNA fragment using Quiagen's PCR Purification kit, it was used as an insertion DNA fragment for vector construction.

On the other hand, the pDZ vector treated with the restriction enzyme SmaI and then heat-treated at 65° C. for 60 minutes and the insertion DNA fragment amplified through PCR were connected using Infusion Cloning Kit, and then transformed into *E. coli* DH5α. The strain was plated on LB solid medium containing kanamycin (25 mg/l). After selecting colonies transformed with the vector into which the desired gene was inserted through PCR using primers of SEQ ID NOs: 20 and 21, a plasmid was obtained using a commonly known plasmid extraction method. The plasmid was named pDZ-gIxR (E45A).

By the same method, pDZ-gIxR (D66A) using primers of SEQ ID NOs: 16 and 28, 17 and 29, pDZ-gIxR (T166D) using primers of SEQ ID NOs: 16 and 34, 17 and 35, and pDZ-gIxR (E168A) using primers of SEQ ID NOs: 16 and 40, 17 and 41 were constructed.

The nucleic acid sequences of the primers used in the present example were described in Table 3 below.

TABLE 3

| Name | Sequence (5'→3') | SEQ ID NO |
|---|---|---|
| glxR L1 | GAATTCGAGCTCGGTACCCTGAGACCCCAC GCGAG | SEQ ID NO: 16 |
| glxR R2 | GACTCTAGAGGATCCCCATCGACGGTGTCA CCCCAC | SEQ ID NO: 17 |
| glxR(E45A) L2 | GTAAAGGCGGTCACCTGGCgCGCCCTCGTC GAAGATGG | SEQ ID NO: 18 |
| glxR(E45A) R1 | CCATCTTCGACGAGGGCGcGCCAGGTGACC GCCTTTAC | SEQ ID NO: 19 |
| pDZ_F | TATTACGCCAGCTGGCGAAAG | SEQ ID NO: 20 |
| pDZ_R | TTCCGGCTCGTATGTTGTGTG | SEQ ID NO: 21 |
| glxR(E45S) L2 | GTAAAGGCGGTCACCTGGagaGCCCTCGTC GAAGATGG | SEQ ID NO: 22 |
| glxR(E45S) R1 | CCATCTTCGACGAGGGCtctCCAGGTGACCG CCTTTAC | SEQ ID NO: 23 |
| glxR(E45F) L2 | GTAAAGGCGGTCACCTGGaaaGCCCTCGTC GAAGATGG | SEQ ID NO: 24 |
| glxR(E45F) R1 | CCATCTTCGACGAGGGCtttCCAGGTGACCGC CTTTAC | SEQ ID NO: 25 |
| glxR(E45K) L2 | GTAAAGGCGGTCACCTGGCTtGCCCTCGTCG AAGATGG | SEQ ID NO: 26 |
| glxR(E45K) R1 | CCATCTTCGACGAGGGCaAGCCAGGTGACC GCCTTTAC | SEQ ID NO: 27 |
| glxR(D66A) L2 | GGTTTTCGCGGCCtgCCGGTGCGTGGCGCG CAAG | SEQ ID NO: 28 |
| glxR(D66A) R1 | GCGCCACGCACCGGcaGGCCGCGAAAACCT GCTG | SEQ ID NO: 29 |
| glxR(D66F) L2 | CAGCAGGTTTTCGCGGCCaaaCGGTGCGTG GCGC | SEQ ID NO: 30 |
| glxR(D66F) R1 | GCGCCACGCACCGtttGGCCGCGAAAACCTG CTG | SEQ ID NO: 31 |
| glxR(D66K) L2 | GGTTTTCGCGGCCtttCCGGTGCGTGGCGCG CAAG | SEQ ID NO: 32 |

TABLE 3-continued

| Name | Sequence (5'→3') | SEQ ID NO |
|---|---|---|
| glxR(D66K) R1 | GCGCCACGCACCGaaaGGCCGCGAAAACCT GCTG | SEQ ID NO: 33 |
| glxR(T166D) L2 | GCCAGCTTCTTGGtcGCCGAAGCGGTTAGCC AGC | SEQ ID NO: 34 |
| glxR(T166D) R1 | AACCGCTTCGGCgaCCAAGAAGCTGGCGCG CTG | SEQ ID NO: 35 |
| glxR(T166F) L2 | GCCAGCTTCTTGGaaGCCGAAGCGGTTAGC CAGC | SEQ ID NO: 36 |
| glxR(T166F) R1 | AACCGCTTCGGCttCCAAGAAGCTGGCGCGC TG | SEQ ID NO: 37 |
| glxR(T166K) L2 | GCCAGCTTCTTGtttGCCGAAGCGGTTAGCCA GC | SEQ ID NO: 38 |
| glxR(T166K) R1 | AACCGCTTCGGCaaaCAAGAAGCTGGCGCG CTG | SEQ ID NO: 39 |
| glxR(E168A) L2 | AGCGCGCCAGCagCTTGGGCGCCGAAGCGG TTAG | SEQ ID NO: 40 |
| glxR(E168A) R1 | CTTCGGCGCCCAAGctGCTGGCGCGCTGCG CGTG | SEQ ID NO: 41 |
| glxR(E168F) L2 | AGCGCGCCAGCaaaTTGGGCGCCGAAGCGG TTAG | SEQ ID NO: 42 |
| glxR(E168F) R1 | CTTCGGCGCCCAAtttGCTGGCGCGCTGCGC GTG | SEQ ID NO: 43 |
| glxR(E168K) L2 | AGCGCGCCAGCcttTTGGGCGCCGAAGCGGT TAG | SEQ ID NO: 44 |
| glxR(E168K) R1 | CTTCGGCGCCCAAaagGCTGGCGCGCTGCG CGTG | SEQ ID NO: 45 |

A total of 4 kinds of vectors pDZ-gIxR (E45A), pDZ-gIxR (D66A), pDZ-gIxR (T166D) and pDZ-gIxR (E168A) comprising a variant polypeptide in which the 45$^{th}$, 66$^{th}$, 166$^{th}$ an 168$^{th}$ amino acids of SEQ ID NO: 1 were substituted with other amino acids were constructed as above, and these vectors are vectors which can substitute the 45$^{th}$ amino acid glutamate (glutamic acid, E) of the GlxR protein into alanine (A), the 66$^{th}$ amino acid aspartate (aspartic acid, D) into alanine (A), the 166$^{th}$ amino acid threonine (T) into aspartate (D), and the 168$^{th}$ amino acid glutamate (E) into alanine (A), respectively.

Example 2: Evaluation of L-Threonine Productivity of gIxR Variant Strain Based on Wildtype *Corynebacterium* sp. Microorganism In the present examples, based on *Corynebacterium glutamicum* ATCC13032, the L-threonine productivity of the gIxR variant strain in which the 45$^{th}$ amino acid glutamate, the 66$^{th}$ amino acid aspartate, the 166$^{th}$ amino acid threonine, and the 168$^{th}$ amino acid glutamate were substituted with alanine, alanine, aspartate and glutamate, respectively, in the amino acid sequence (SEQ ID NO: 1) of the wildtype GlxR protein endogenously possessed by the ATCC13032 strain, was tried to be evaluated.

The pDZ-gIxR (E45A), pDZ-gIxR (D66A), pDZ-gIxR (T166D) and pDZ-gIxR (E168A) vectors constructed in Example 1 were transformed by electric pulse method. The strains in which a heterogenous nucleotide substitution mutation was introduced into the gIxR gene in this way were named ATCC13032 ΔgIxR::gIxR (E45A), ATCC13032 ΔgIxR::gIxR (D66A), ATCC13032 ΔgIxR::gIxR (T166D), ATCC13032 ΔgIxR::gIxR (E168A), respectively. 4 strains constructed using the ATCC13032 strain as a control group [ATCC13032 ΔgIxR::gIxR (E45A), ATCC13032 ΔgIxR::gIxR (D66A), ATCC13032 ΔgIxR::gIxR (T166D), ATCC13032 ΔgIxR::gIxR (E168A)] were cultured in the following method to measure the rate of sugar consumption, and threonine and lysine production yield.

At first, each strain was inoculated in a 250 ㎖ corner-baffled flask containing seed medium 25 ㎖, and was cultured with shaking at 200 rpm at 30° C. for 20 hours. Then, 1㎖ seed culture solution was inoculated in a 250 ㎖ corner-baffled flask containing production medium 24 ㎖, and was cultured with shaking at 200 rpm at 32° C. for 24 hours. The composition of the seed medium and production medium was described in Table 4 below, respectively. After completing culturing, the concentration of L-lysine and L-threonine was measured using HPLC (Waters 2478), and the equivalent remaining in the medium (residual equivalent) was analyzed using Biochemistry analyzer (YSI 2900) to measure the rate of sugar consumption, and the result was shown in Table 5.

TABLE 4

| Medium type | Component |
|---|---|
| Seed medium (pH 7.0) | Glucose 20 g, peptone 10 g, yeast extract 5 g, urea 1.5 g, $KH_2PO_4$ 4 g, $K_2HPO_4$ 8 g, $MgSO_4$•$7H_2O$ 0.5 g, biotin 100 μg, thiamine HCl 1000 μg, calcium-pantothenic acid 2000 μg, nicotinamide 2000 μg (based on distilled water 1 liter) |
| L-THREONINE production medium (pH 7.2) | Glucose 30 g, $KH_2PO_4$ 2 g, Urea 3 g, $(NH_4)_2SO_4$ 40 g, Peptone 2.5 g, CSL(Sigma) 5 g(10 ml), $MgSO_4$•$7H_2O$ 0.5 g, Leucine 400 mg, $CaCO_3$ 20 g (based on distilled water 1 liter) |

TABLE 5

| Strain | L-Thr concentration (g/L) | Rate of sugar consumption (g/hr) | L-LYS concentration (g/L) |
|---|---|---|---|
| ATCC13032 | 0 | 3.65 | 1.2 |
| ATCC13032 ΔglxR::glxR* (E45A) | 0.22 | 4.22 | 0 |
| ATCC13032 ΔglxR::glxR* (D66A) | 0.16 | 3.98 | 0.2 |
| ATCC13032 ΔglxR::glxR* (T166D) | 0.1 | — | 1 |
| ATCC13032 ΔglxR::glxR* (E168A) | 0.06 | — | 0.7 |

As shown in Table 5, when the $45^{th}$, $66^{th}$, $166^{th}$ and $168^{th}$ amino acids of the GlxR protein were substituted, respectively, compared to the *Corynebacterium glutamicum* ATC13032 strain, the concentration of the produced L-threonine was increased and the concentration of the by-product L-lysine was reduced.

In addition, as shown in Table 5, it could be confirmed that the rate of sugar consumption was also improved, when the $45^{th}$ or $66^{th}$ amino acid of Glx protein was substituted with alanine. Accordingly, as the strain in which the variant in which the $45^{th}$ or $68^{th}$ amino acid was substituted with alanine compared to the mother strain (E45A or D66A) had the faster rate of sugar consumption, the time it takes to produce the same amount of L-threonine was shortened, and the L-threonine productivity was improved.

Example 3: Construction of Vector Library in which the 45, 66, 166 and $168^{th}$ Amino Acid of gIxR Gene were Substituted with Amino Acids of Different Properties It was confirmed that the rate of sugar consumption and productivity of L-threonine were improved, when the 45, 66, 166 and $168^{th}$ amino acids of the GlxR protein were substituted with other amino acids each in Example 2. In order to further confirm the effect when the 45, 66, 166 and $168^{th}$ amino acids of the GlxR protein (SEQ ID NO: 1) were substituted with amino acids of other properties, substitution of the wildtype amino acids with amino acids comprising the mutation was tried. In order to introduce a total of 13 kinds of heterogenous nucleotide substitution mutations comprising E45A, D66A, T166D and E168A mutations confirmed in Example 2, each recombinant vector was constructed by the same method as Example 1.

pDZ-gIxR (E45S) using primers of SEQ ID NOs: 16 and 22, 17 and 23, pDZ-gIxR (E45F) using primers of SEQ ID NOs: 16 and 24, 17 and 25, pDZ-gIxR (E45K) using primers of SEQ ID NOs: 16 and 26, 17 and 27, pDZ-gIxR (D66F) using primers of SEQ ID NOs: 16 and 30, 17 and 31, pDZ-gIxR (D66K) using primers of SEQ ID NOs: 16 and 32, 17 and 33, pDZ-gIxR (T166F) using primers of SEQ ID NOs: 16 and 36, 17 and 37, pDZ-gIxR (T166K) using primers of SEQ ID NOs: 16 and 38, 17 and 39, pDZ-gIxR (E168F) using primers of SEQ ID NOs: 16 and 42, 17 and 43, and pDZ-gIxR (E168K) using primers of SEQ ID NOs: 16 and 44, 17 and 45 were constructed, respectively. The nucleic acid sequences of the primers used in the present example were described in Table 3 above.

Example 4: Analysis of L-Threonine Productivity for the 45, 66, 166 and 168th Amino Acid Variants of gIxR Gene Based on Wildtype *Corynebacterium* sp. Microorganism The vector library constructed in Example 3 was transformed into the ATC13032 strain by electric pulse method. The strains in which a heterogenous nucleotide substitution mutation was introduced into the gIxR gene in this way were named ATCC13032 ΔgIxR::gIxR* (E45S), ATCC13032 ΔgIxR::gIxR* (E45F), ATCC13032 ΔgIxR::gIxR* (E45K), ATCC13032 ΔgIxR::gIxR* (D66F), ATCC13032 ΔgIxR::gIxR* (D66K), ATCC13032 ΔgIxR::gIxR* (T166F), ATCC13032 ΔgIxR::gIxR* (T166K), ATCC13032 ΔgIxR::gIxR* (E168F), and ATCC13032 ΔgIxR::gIxR* (E168K).

The ATCC13032 strain was used as a control group and cultured by the same method as Example 2 to measure the productivity of L-threonine and L-lysine and rate of sugar consumption, and the result was described in Table 6.

TABLE 6

| Strain | L-Thr concentration (g/L) | Rate of sugar consumption (g/hr) | L-LYS concentration (g/L) |
|---|---|---|---|
| ATCC13032 | 0 | 3.47 | 0.4 |
| ATCC13032 ΔglxR::glxR* (E45A) | 0.2 | 4.02 | 0.4 |
| ATCC13032 ΔglxR::glxR* (E45S) | 0.1 | 3.50 | 0.3 |
| ATCC13032 ΔglxR::glxR* (E45F) | 0.1 | — | 0.4 |
| ATCC13032 ΔglxR::glxR* (E45K) | 0.07 | 3.66 | 0.3 |
| ATCC13032 ΔglxR::glxR* (D66A) | 0.22 | 3.76 | 0.2 |
| ATCC13032 ΔglxR::glxR* (D66F) | 0.11 | — | 0.1 |
| ATCC13032 ΔglxR::glxR* (D66K) | 0.06 | — | 0.4 |
| ATCC13032 ΔglxR::glxR* (T166D) | 0.18 | 3.86 | 0.4 |
| ATCC13032 ΔglxR::glxR* (T166F) | 0.07 | — | 0.3 |
| ATCC13032 ΔglxR::glxR* (T166K) | 0.04 | 3.52 | 0.3 |
| ATCC13032 ΔglxR::glxR* (E168A) | 0.15 | 3.81 | 0.3 |
| ATCC13032 ΔglxR::glxR* (E168F) | 0.1 | — | 0.2 |
| ATCC13032 ΔglxR::glxR* (E168K) | 0.05 | — | 0.1 |

As the experimental result, when the 45$^{th}$ amino acid glutamate in the GlxR protein (SEQ ID NO: 1) was substituted with alanine, serine, phenylalanine or lysine, the L-threonine (Thr) productivity was given to the strain, and the rate of sugar consumption was improved, and the production of by-products such as lysine was reduced. In addition, when the 66$^{th}$ amino acid aspartate in the GlxR protein (SEQ ID NO: 1) was substituted with alanine, phenylalanine or lysine, the L-threonine productivity was given to the strain, and the rate of sugar consumption was improved, and the production of by-products such as lysine was reduced. Furthermore, when the 166$^{th}$ amino acid threonine in the GlxR protein (SEQ ID NO: 1) was substituted with aspartate, phenylalanine or lysine, the L-threonine productivity was given to the strain, and the rate of sugar consumption was improved, and the production of by-products such as lysine was reduced. Moreover, when the 168$^{th}$ amino acid glutamate in the GlxR protein (SEQ ID NO: 1) was substituted with alanine, phenylalanine or lysine, the L-threonine productivity was given to the strain, and the rate of sugar consumption was improved, and the production of by-products such as lysine was reduced.

Example 5: Analysis of L-Threonine Productivity and Growth Rate for gIxR Variant Strain Based on Threonine Producing Strain In the present example, in order to clearly examine the threonine concentration and growth rate according to the gIxR mutation introduction, the productivity of L-threonine was tried to be evaluated by introducing 4 kinds of vectors constructed in Example 1 into a L-threonine producing strain. In order to construct a L-threonine producing strain, by changing the 1128$^{th}$ to 1131$^{th}$ nucleotide sequence of the gene encoding wildtype LysC protein from conventional TTG to AAG to solve feedback inhibition of LysC (aspartate kinase) acting as the first important enzyme in the threonine synthesis pathway from wildtype *Corynebacterium glutamicum* ATCC13032, a strain in which a variant LysC (L377K) mutation, in which the 377$^{th}$ amino acid leucine from the N-terminus of the wildtype LysC protein was substituted with lysine, was introduced was constructed. The amino acid sequence of LysC (L377K) was described in Table 7 below as SEQ ID NO: 46.

The recombinant vector for mutation introduction was constructed by the following method. In order to construct strains in which LysC (L377K) mutation was introduced, primers of SEQ ID NOs: 47 and 48 in which a restriction enzyme SmaI recognition site was inserted into the 5' fragment and 3' fragment at the position about 500 bp away, back and forth, respectively, from the 1128 to 1131th position of the lysC gene using genome DNA extracted from the ATCC13032 strain were synthesized. To introduce LysC (L377K) heterogenous nucleotide substitution mutation, primers of SEQ ID NOs: 49 and 50 to substitute the 1128 to 1131th nucleotide sequence of the lysC gene were synthesized.

Specifically, the pDZ-lysC (L377K) plasmid was constructed in a form in which DNA fragments (515, 538 bp each) positioned at the 5' and 3' terminuses of the lysC gene were connected to the pDZ vector. The 5' terminal gene fragment was constructed using primers of SEQ ID NOs: 47 and 49 using the chromosome of the ATCC13032 strain as a template through PCR. PCR conditions were repeating denaturation at 94° C. for 5 minutes, denaturation at 94° C. for 1 minute, annealing at 56° C. for 1 minute, and polymerization at 72° C. for 40 seconds, 30 times, and then performing polymerization at 72° C. for 10 minutes. By the same method, the gene fragment positioned at the 3' terminus of the lysC gene was constructed using SEQ ID NOs: 48 and 50 through PCR. After purifying the amplified DNA fragment using Quiagen's PCR Purification kit, it was used as an insertion DNA fragment for vector construction.

On the other hand, the pDZ vector treated with the restriction enzyme SmaI and then heat-treated at 65° C. for 20 minutes and the insertion DNA fragment amplified through PCR were connected using Infusion Cloning Kit, and then transformed into *E. coli* DH5α. The strain was plated on LB solid medium containing kanamycin (25 mg/l). After selecting colonies transformed with the vector into which the desired gene was inserted through PCR using primers of SEQ ID NOs: 47 and 48, a plasmid was obtained using a commonly known plasmid extraction method. The plasmid was named pDZ-lysC (L377K). The nucleic acid sequence of the primers used in the present example was described in Table 7 below.

TABLE 7

| Name | Sequence | SEQ ID NO |
|---|---|---|
| LysC_L377K | MALVVQKYGGSSLESAERIRNVAERIVATKKAGND VVVVCSAMGDTTDELLELAAAVNPVPPAREMDML LTAGERISNALVAMAIESLGAEAQSFTGSQAGVLT TERHGNARIVDVTPGRVREALDEGKICIVAGFQGV NKETRDVTTLGRGGSDTTAVALAAALNADVCEIYS DVDGVYTADPRIVPNAQKLEKLSFEEMLELAAVGS KILVLRSVEYARAFNVPLRVRSSYSNDPGTLIAGS MEDIPVEEAVLTGVATDKSEAKVTVLGISDKPGEA AKVFRALADAEINIDMVLQNVSSVEDGTTDITFTCP RSDGRRAMEILKKLQVQGNWTNVLYDDQVGKVSL VGAGMKSHPGVTAEFMEALRDVNVNIEKISTSEIRI SVLIREDDLDAAARALHEQFQLGGEDEAVVYAGT GR | SEQ ID NO: 46 |
| LysC L1 | TCGAGCTCGGTACCCGCTGCGCAGTGTTGAATA C | SEQ ID NO: 47 |
| LysC R2 | CTCTAGAGGATCCCCGTTCACCTCAGAGACGAT T | SEQ ID NO: 48 |
| lysC(L377K) L2 | TGGAAATCTTTTCGATGTTCACGTTGACAT | SEQ ID NO: 49 |
| lysC(L377K) R1 | ATGTCAACGTGAACATCGAAAAGATTTCC | SEQ ID NO: 50 |

The pDZ-lysC (L377K) constructed above was transformed into the *Corynebacterium glutamicum* ATCC13032 strain by electric pulse method. The strain in which a heterogenous nucleotide substitution mutation was introduced into the lysC gene in this way was named CJP1. The CJP1 was named CA01-2307, and it was deposited to Korean Culture Center of Microorganisms (KCCM) which is an international depository authority under the Budapest Treaty, and it was given an accession number KCCM12000P.

To the KCCM12000P strain constructed above, mutation was introduced into a gene encoding homoserine dehydrogenase (Hom) producing homoserine which is a common intermediate of the biosynthesis pathway of L-threonine and L-isoleucine. Specifically, by substituting the 1218 to 1221th nucleotide sequence of the gene encoding wildtype homoserine dehydrogenase from TTG to AAG, the strain in which variant Hom (R407H) mutation in a form in which the 407$^{th}$ amino acid from the N-terminus of wildtype homoserine dehydrogenase, arginine was substituted with histidine was constructed. The amino acid sequence of Hom (R407H) was described in Table 8 below as SEQ ID NO: 51. The recombinant vector for mutation introduction was constructed by the following method.

At first, primers of SEQ ID NOs: 52 and 53 in which a restriction enzyme SaII recognition site was inserted to the 5' fragment and 3' fragment at the position about 600 bp away, back and forth, respectively, from the 1219 to 1221th position of the hom gene using genome DNA extracted from the ATCC13032 strain as a template were synthesized. To introduce Hom (R407H) heterogenous nucleotide substitution mutation, primers of SEQ ID NOs: 54 and 55 to substitute the 1219 to 1221th nucleotide sequence of the hom gene were synthesized.

Specifically, the pDZ-hom (R407H) plasmid was constructed in a form in which DNA fragments (600 bp each) positioned at the 5' and 3' terminuses of the hom gene. The 5' terminal gene fragment was constructed using primers of SEQ ID NOs: 52 and 54 using chromosome of the WT strain through PCR. PCR conditions were repeating denaturation at 94° C. for 2 minutes, denaturation at 94° C. for 1 minute, annealing at 56° C. for 1 minute, and polymerization at 72° C. for 40 seconds, 30 times, and then performing polymerization at 72° C. for 10 minutes. By the same method, the gene fragment positioned at the 3' terminus of the hom gene was constructed using SEQ ID NOs: 53 and 55 through PCR. After purifying the amplified DNA fragment using Quiagen's PCR Purification kit, it was used as an insertion DNA fragment for vector construction.

On the other hand, the pDZ vector treated with the restriction enzyme SaII and then heat-treated at 65° C. for 20 minutes and the insertion DNA fragment amplified through PCR were connected using Infusion Cloning Kit, and then transformed into *E. coli* DH5α. The strain was plated on LB solid medium containing kanamycin (25 mg/l). After selecting colonies transformed with the vector into which the desired gene was inserted through PCR using primers of SEQ ID NOs: 52 and 53, a plasmid was obtained using a commonly known plasmid extraction method. The plasmid was named pDZ-hom (R407H). The nucleic acid sequence of the primers used in the present example was described in Table 8 below.

TABLE 8

| Name | Sequence | SEQ ID NO |
|---|---|---|
| Hom_R407H | MTSASAPSFNPGKGPGSAVGIALLGFGTVGTEV MRLMTEYGDELAHRIGGPLEVRGIAVSDISKPRE GVAPELLTEDAFALIEREDVDIVVEVIGGIEYPREV VLAALKAGKSVVTANKALVAAHSAELADAAEAAN VDLYFEAAVAGAIPVVGPLRRSLAGDQIQSVMGIV NGTTNFILDAMDSTGADYADSLAEATRLGYAEAD PTADVEGHDAASKAAILASIAFHTRVTADDVYCE GISNISAADIEAAQQAGHTIKLLAICEKFTNKEGKS | SEQ ID NO: 51 |

TABLE 8-continued

| Name | Sequence | SEQ ID NO |
|---|---|---|
| | AISARVHPTLLPVSHPLASVNKSFNAIFVEAEAAG RLMFYGNGAGGAPTASAVLGDVVGAARNKVHG GRAPGESTYANLPIADFGETTTRYHLDMDVEDRV GVLAELASLFSEQGISLRTIRQEERDDDAHLIVVT HSALESDLSRTVELLKAKPVVKAINSVIRLERD | |
| hom L1 | ATCCTCTAGAGTCGACCCAACTGCAGACGTCG AA | SEQ ID NO: 52 |
| hom R2 | ATGCCTGCAGGTCGACATAGACAGATTTGTCC ACG | SEQ ID NO: 53 |
| hom(R407H) L2 | GTGACCACGATCAGATGTGCATCATCATCGCG CTC | SEQ ID NO: 54 |
| hom(R407H) R1 | GCGATGATGATGCACATCTGATCGTGGTCACC CAC | SEQ ID NO: 55 |

The pDZ-hom (R407H) constructed above was transformed into KCCM12000P by electric pulse method. The strain in which a heterogenous nucleotide substitution mutation was introduced into the hom gene in this way was named KCCM12000P-R398Q, and it was deposited to Korean Culture Center of Microorganisms (KCCM) which is an international depository authority under the Budapest Treaty, and it was given an accession number KCCM12120P (Korean Patent No. 10-1947959).

The pDZ-gIxR (E45A), pDZ-gIxR (D66A), pDZ-gIxR (T166D) and pDZ-gIxR (E168A) vectors constructed in Example 1 were transformed to the KCCM12120P strain by electric pulse method, respectively. The strain in which nucleotide substitution mutation was introduced to the gIxR gene was constructed, and KCCM12120P ΔgIxR::gIxR* (E45A) was named CA09-2373, and KCCM12120P ΔgIxR::gIxR* (D66A) was named CA09-2374, and KCCM12120P ΔgIxR::gIxR* (T166D) was named CA09-2325, and KCCM12120P ΔgIxR::gIxR* (E168A) was named CA09-2324, respectively.

A total of 4 kinds of gIxR variants were cultured by the following method using a L-threonine producing strain, KCCM12120P strain, to measure the L-threonine production yield, rate of sugar consumption and production concentration of by-products such as L-lysine.

Each strain was inoculated in a 250 ㎖ corner-baffled flask containing seed medium 25 ㎖, and was cultured with shaking at 200 rpm at 30° C. for 20 hours. Then, 1㎖ seed culture solution was inoculated in a 250 ㎖ corner-baffled flask containing production medium 24 ㎖, and was cultured with shaking at 200 rpm at 32° C. for 48 hours. The composition of the seed medium and production medium was described in Table 9 below, respectively. After completing culturing, the concentration of L-lysine and L-threonine and rate of sugar consumption were measured using HPLC and Biochemistry analyzer (YSI 2900), and the result was shown in Table 10.

TABLE 9

| Medium type | Component |
|---|---|
| Seed medium (pH 7.0) | Glucose 20 g, peptone 10 g, yeast extract 5 g, urea 1.5 g, $KH_2PO_4$ 4 g, $K_2HPO_4$ 8 g, $MgSO_4$•$7H_2O$ 0.5 g, biotin 100 μg, thiamine HCl 1000 μg, calcium-pantothenic acid 2000 μg, nicotinamide 2000 μg (based on distilled water 1 liter) |
| L-THREONINE production medium (pH 7.0) | Glucose 100 g, $KH_2PO_4$ 2 g, Urea 3 g, $(NH_4)_2SO_4$ 25 g, Peptone 2.5 g, CSL(Sigma) 5 g(10 ml), $MgSO_4$•$7H_2O$ 0.5 g, biotin 100 μg, thiamine HCl 1000 μg, calcium-pantothenic acid 2000 μg, nicotinamide 3000 μg, $CaCO_3$ 30 g (based on distilled water 1 liter) |

TABLE 10

| Strain | L-Thr concentration (g/L) | Rate of sugar consumption (g/hr) | L-LYS concentration (g/L) |
|---|---|---|---|
| KCCM12120P | 7.62 | 4.04 | 0.36 |
| CA09-2373 | 9.23 | 4.66 | 0.28 |
| CA09-2374 | 9.67 | 4.21 | 0.31 |
| CA09-2325 | 8.87 | 4.13 | 0.35 |
| CA09-2324 | 8.90 | 4.22 | — |

As shown in Table 10, as the result of measuring the production concentration of L-threonine and by-products (L-lysine) by culturing 4 kinds of gIxR variant strains (CA09-2373, CA09-2374, CA09-2325, CA09-2324) using the L-threonine producing strain, KCCM12120P strain as a control group, it could be confirmed that all 4 kinds of strains in which the substitution mutation was introduced to the gIxR gene reduced the production of other by-products including L-lysine or there was no big change compared to the control group, but the production of L-threonine was significantly increased. In addition, it could be confirmed that in all CA09-2373, CA09-2374, CA09-2325, and CA09-2324 strains, compared to the control group, the rate of sugar consumption was improved, and the time it took to produce the same amount of L-threonine was shortened and the L-threonine productivity was improved.

The CA09-2373, CA09-2374, CA09-2325 and CA09-2324 strains were deposited to Korean Culture Center of Microorganisms (KCCM) which is an international depository authority under the Budapest Treaty, and they were given accession numbers KCCM12901P, KCCM12902P, KCCM12900P, and KCCM12899P, respectively.

Accession Number

Depository authority name: Korean Culture Center of Microorganisms (overseas)
Accession number: KCCM12899P
Accession date: 20201217
Depository authority name: Korean Culture Center of Microorganisms (overseas)
Accession number: KCCM12900P
Accession date: 20201217
Depository authority name: Korean Culture Center of Microorganisms (overseas)
Accession number: KCCM12901P
Accession date: 20201217
Depository authority name: Korean Culture Center of Microorganisms (overseas)
Accession number: KCCM12902P
Accession date: 20201217

The invention claimed is:

1. A glyoxylate bypass regulator (GlxR) protein variant, comprising the amino acid sequence at least 95% identical to the amino acid sequence of SEQ ID NO: 1 and further comprising at least one mutation selected from the group consisting of (1) to (4) below:

(1) substitution of the residue corresponding to the 45th amino acid of SEQ ID NO: 1 with alanine, serine, phenylalanine or lysine;

(2) substitution of the residue corresponding to the 66th amino acid of SEQ ID NO: 1 with alanine, phenylalanine or lysine;

(3) substitution of the residue corresponding to the 166th amino acid of SEQ ID NO: 1 with aspartic acid, phenylalanine or lysine; and (4) substitution of the residue corresponding to the 168th amino acid of SEQ ID NO: 1 with alanine, phenylalanine or lysine.

2. A polynucleotide, encoding the GlxR protein variant of claim 1.

3. A microorganism, comprising at least one selected from the group consisting of the GlxR protein variant of claim 1 and a polynucleotide encoding the GlxR protein variant.

4. The microorganism according to claim 3, wherein the microorganism has L-threonine productivity.

5. The microorganism according to claim 3, wherein the microorganism is *Corynebacterium* sp.

6. The microorganism according to claim 5, wherein the *Corynebacterium* sp. microorganism is *Corynebacterium glutamicum*.

7. A method for producing L-threonine, comprising culturing the microorganism of claim 3 in a medium.

8. The method according to claim 7, wherein the method further comprises recovering L-threonine from the cultured medium or microorganism.

9. The method according to claim 7, wherein the microorganism is *Corynebacterium* sp.

10. The method according to claim 9, wherein the *Corynebacterium* sp. microorganism is *Corynebacterium glutamicum.*

11. The GlxR protein variant according to claim 1, wherein the variant comprises the amino acid sequence at least 98% identical to the amino acid sequence of SEQ ID NO: 1.

12. The GlxR protein variant according to claim 1, wherein the variant comprises (1) the substitution of the residue corresponding to the 45th amino acid of SEQ ID NO: 1 with alanine, serine, phenylalanine or lysine.

13. The GlxR protein variant according to claim 1, wherein the variant comprises (2) the substitution of the residue corresponding to the 66th amino acid of SEQ ID NO: 1 with alanine, phenylalanine or lysine.

14. The GlxR protein variant according to claim 1, wherein the variant comprises (3) the substitution of the residue corresponding to the 166th amino acid of SEQ ID NO: 1 with aspartic acid, phenylalanine or lysine.

15. The GlxR protein variant according to claim 1, wherein the variant comprises (4) the substitution of the residue corresponding to the 168th amino acid of SEQ ID NO: 1 with alanine, phenylalanine or lysine.

16. A method for producing L-threonine, comprising culturing the microorganism comprising at least one selected from the group consisting of the GlxR protein variant of claim 11 and a polynucleotide encoding the GlxR protein variant in a medium.

17. The method according to claim 16, wherein the microorganism is *Corynebacterium* sp.

18. A method for producing L-threonine, comprising culturing the microorganism comprising at least one selected from the group consisting of the GlxR protein variant of claim 13 and a polynucleotide encoding the GlxR protein variant in a medium.

19. The method according to claim 18, wherein the microorganism is *Corynebacterium* sp.

20. A method of increasing production of L-threonine, comprising modifying a microorganism to contain at least one selected from the group consisting of the GlxR protein variant of claim 1 and a polynucleotide encoding the GIxR protein variant, and culturing the microorganism in a medium.

* * * * *